(12) United States Patent
Manson et al.

(10) Patent No.: US 11,963,887 B2
(45) Date of Patent: Apr. 23, 2024

(54) EXPANDABLE CAGE ADJUSTMENT TOOL AND METHOD

(71) Applicant: Medos International Sarl, Le Locle (CH)

(72) Inventors: Alec Manson, Boston, MA (US); Sean Saidha, Franklin, MA (US); Connor Engstrom, Hopkinton, MA (US)

(73) Assignee: Medos International Sarl

( * ) Notice: Subject to any disclaimer, the term of this patent is extended or adjusted under 35 U.S.C. 154(b) by 553 days.

(21) Appl. No.: 16/920,992

(22) Filed: Jul. 6, 2020

(65) Prior Publication Data

US 2022/0000639 A1 Jan. 6, 2022

(51) Int. Cl.
*A61F 2/46* (2006.01)
*A61F 2/44* (2006.01)

(52) U.S. Cl.
CPC ............ *A61F 2/4611* (2013.01); *A61F 2/442* (2013.01); *A61F 2002/4627* (2013.01); *A61F 2002/4629* (2013.01)

(58) Field of Classification Search
CPC .................... A61F 2/442; A61F 2/4611; A61F 2002/4627; A61F 2002/4629
See application file for complete search history.

(56) References Cited

U.S. PATENT DOCUMENTS

| 9,889,019 B2 | 2/2018 | Rogers et al. |
| 2007/0185375 A1* | 8/2007 | Stad ..................... A61B 17/025 600/101 |
| 2012/0265259 A1* | 10/2012 | LaPosta ............ A61B 17/8894 606/86 A |
| 2016/0089247 A1 | 3/2016 | Nichols et al. |
| 2018/0125677 A1* | 5/2018 | Burrows-Ownbey ....................... A61F 2/447 |
| 2020/0015985 A1 | 1/2020 | Rogers et al. |

FOREIGN PATENT DOCUMENTS

WO 2014/186384 A2 11/2014

\* cited by examiner

*Primary Examiner* — Nicholas J Plionis
(74) *Attorney, Agent, or Firm* — BakerHostetler

(57) ABSTRACT

An adjustment tool configured to adjust an intervertebral implant comprises a housing, a traveler member, a tether member, and a drive member. The traveler member is coupled to the housing. A proximal end of the tether member is coupled to the traveler, and a distal end of the tether member is configured to couple to the implant. The tether member is substantially linearly fixed to the traveler and rotatable relative to the traveler. The drive member is configured to transition between 1.) a first position in which the drive member is coupled to the tether such that rotation of the drive member causes rotation of the tether relative to the traveler, and 2.) a second position in which the drive member is coupled to the traveler such that rotation of the drive member causes rotation of the traveler relative to the housing.

18 Claims, 25 Drawing Sheets

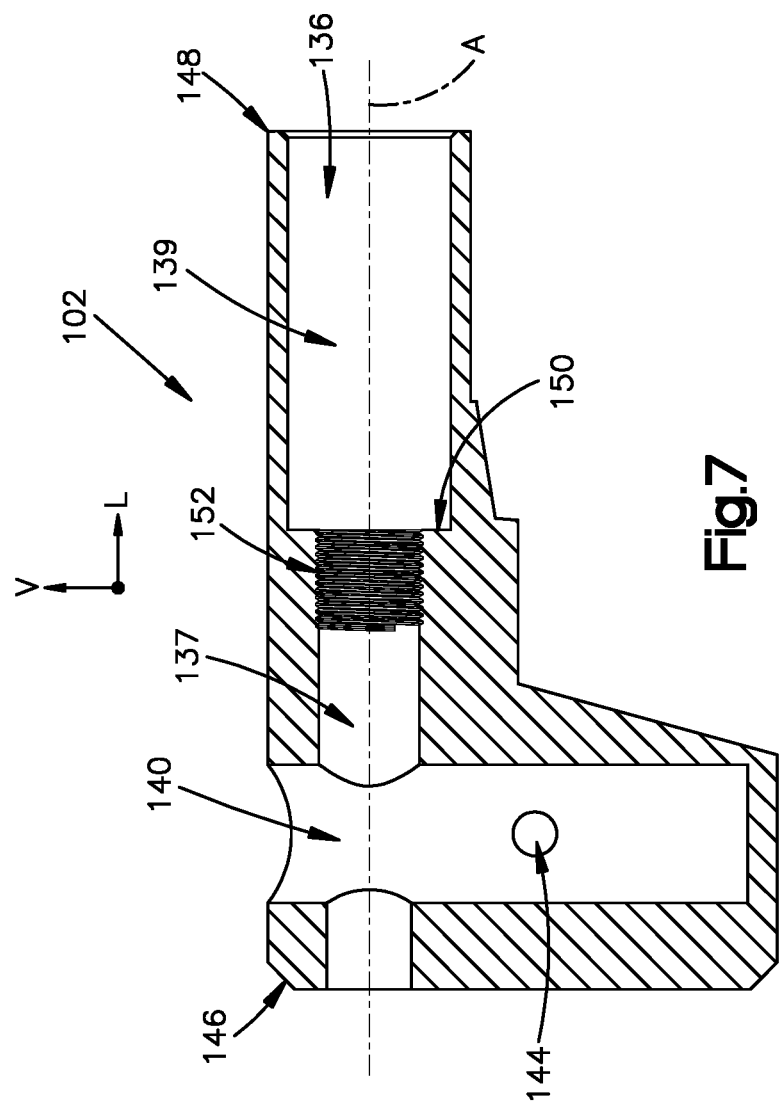
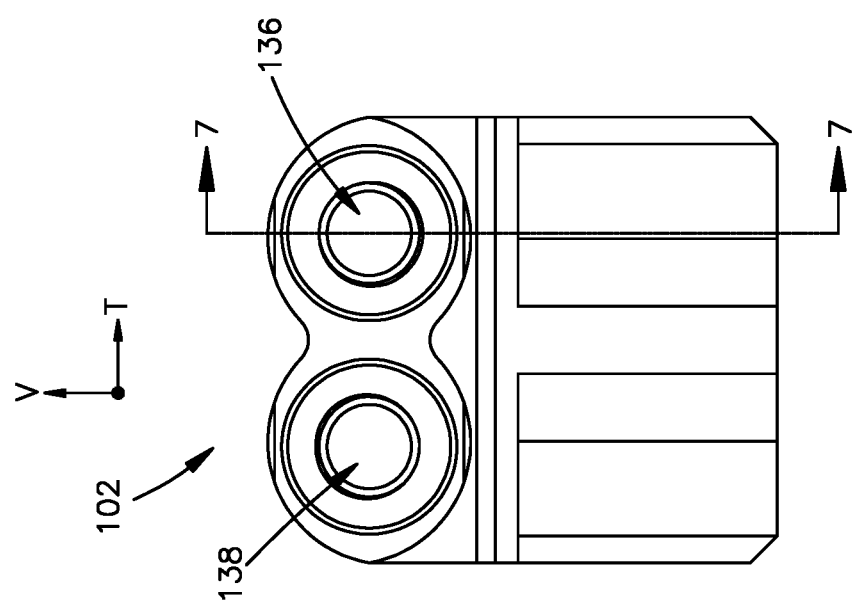

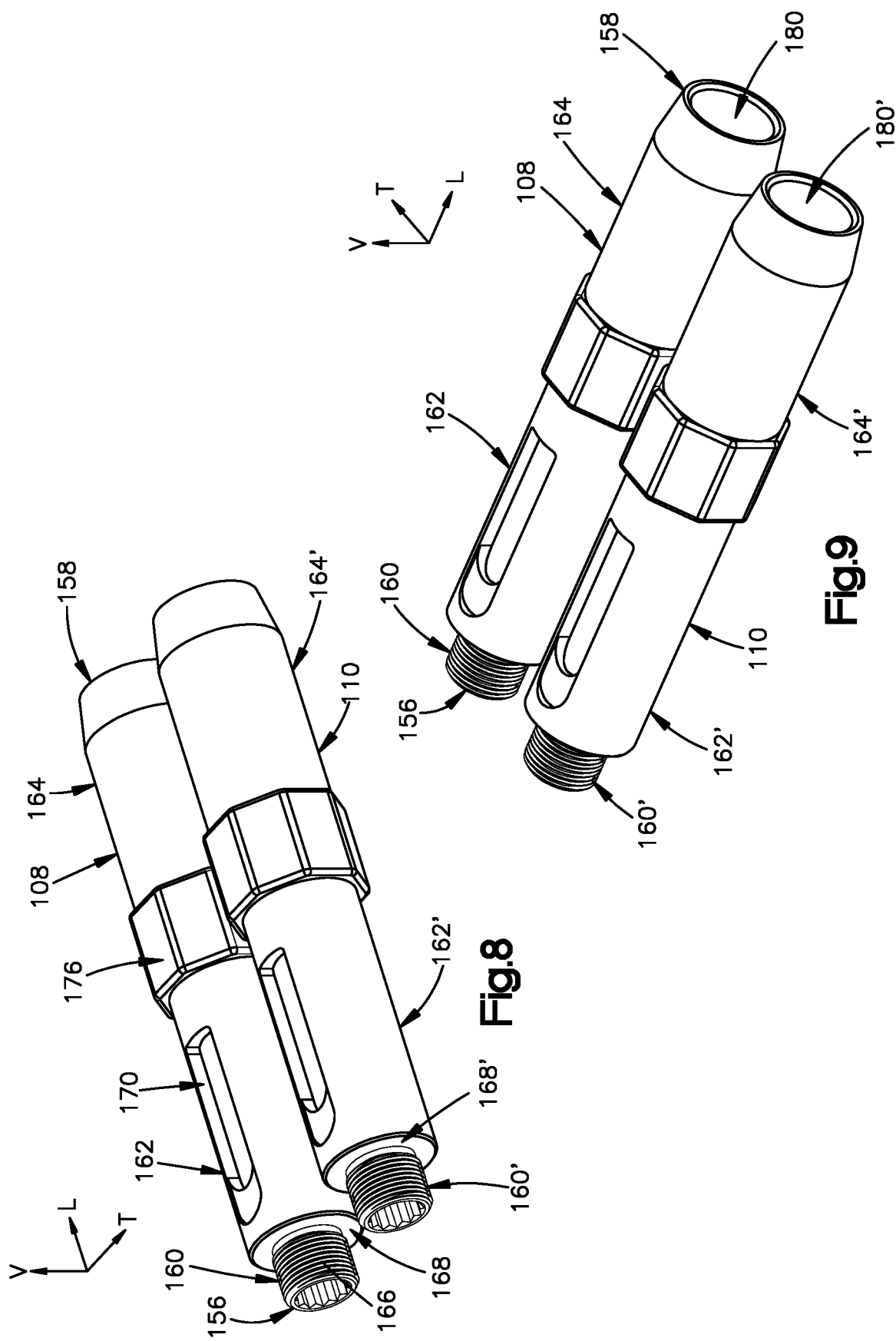

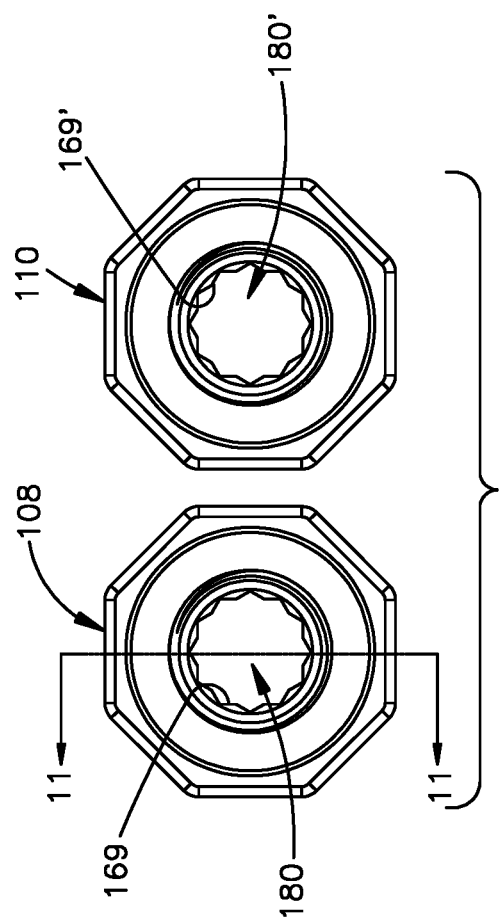
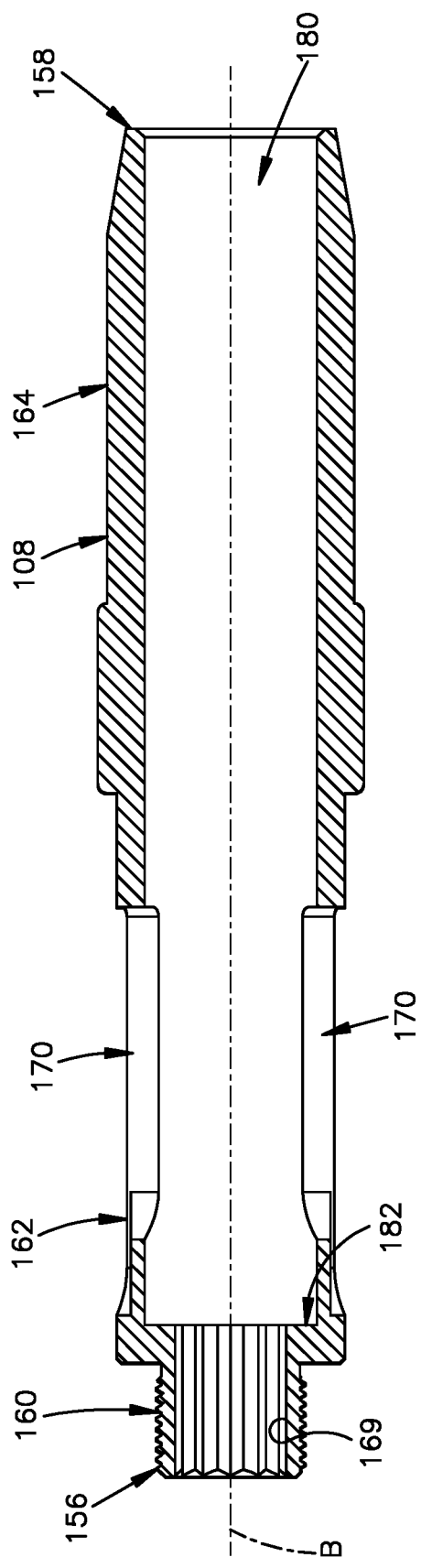

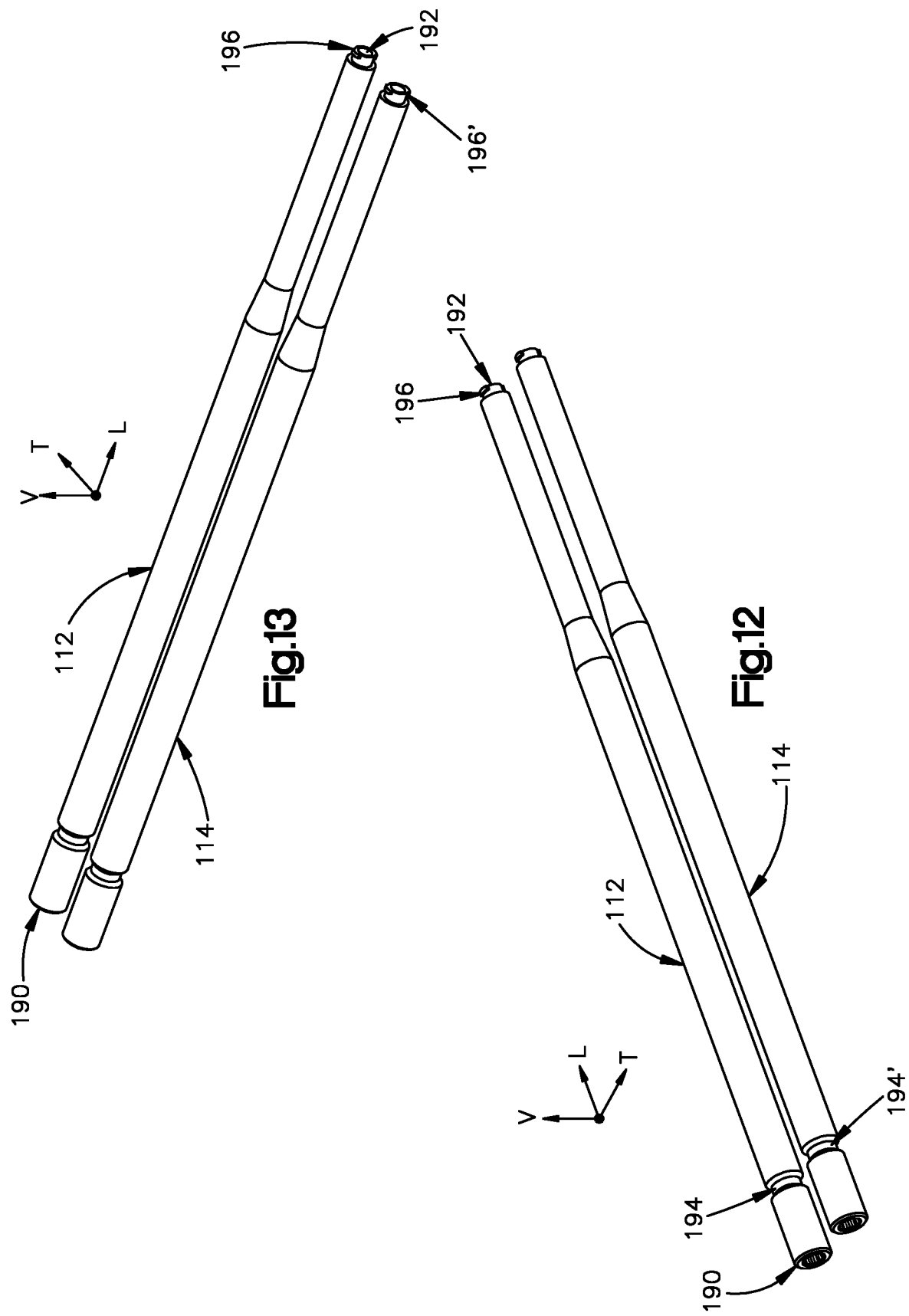

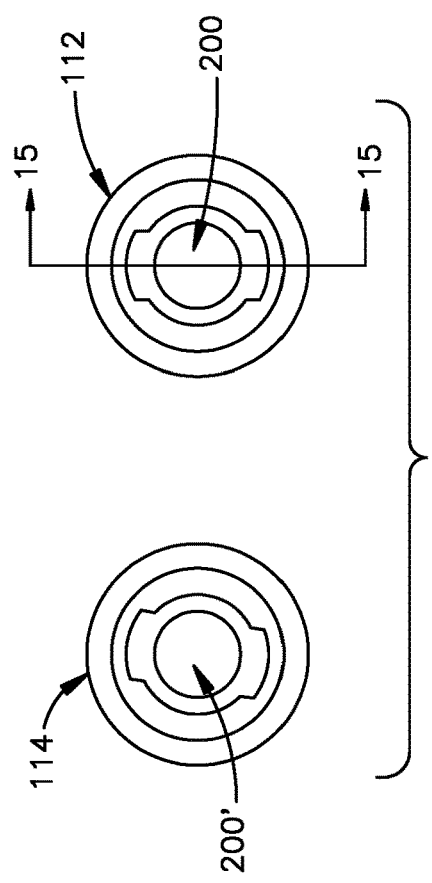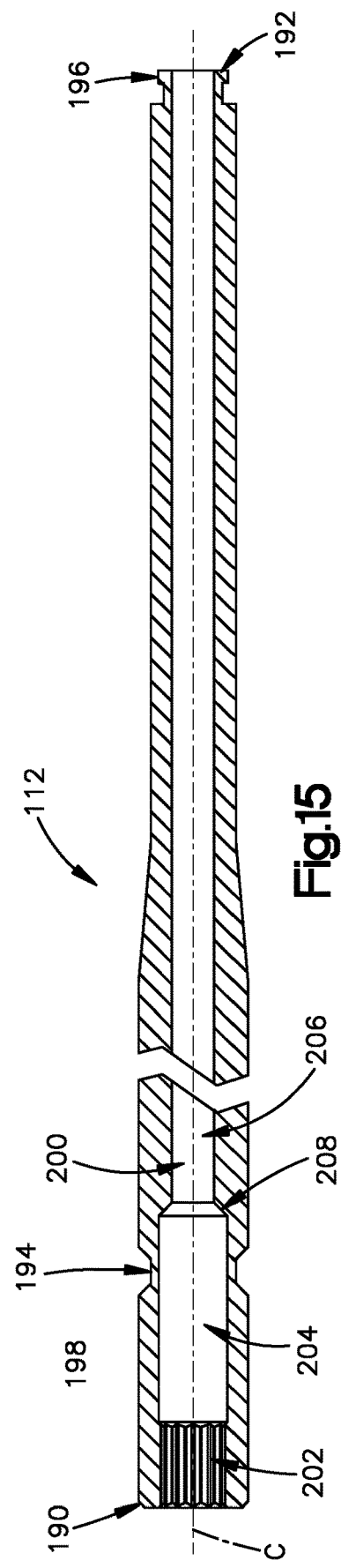

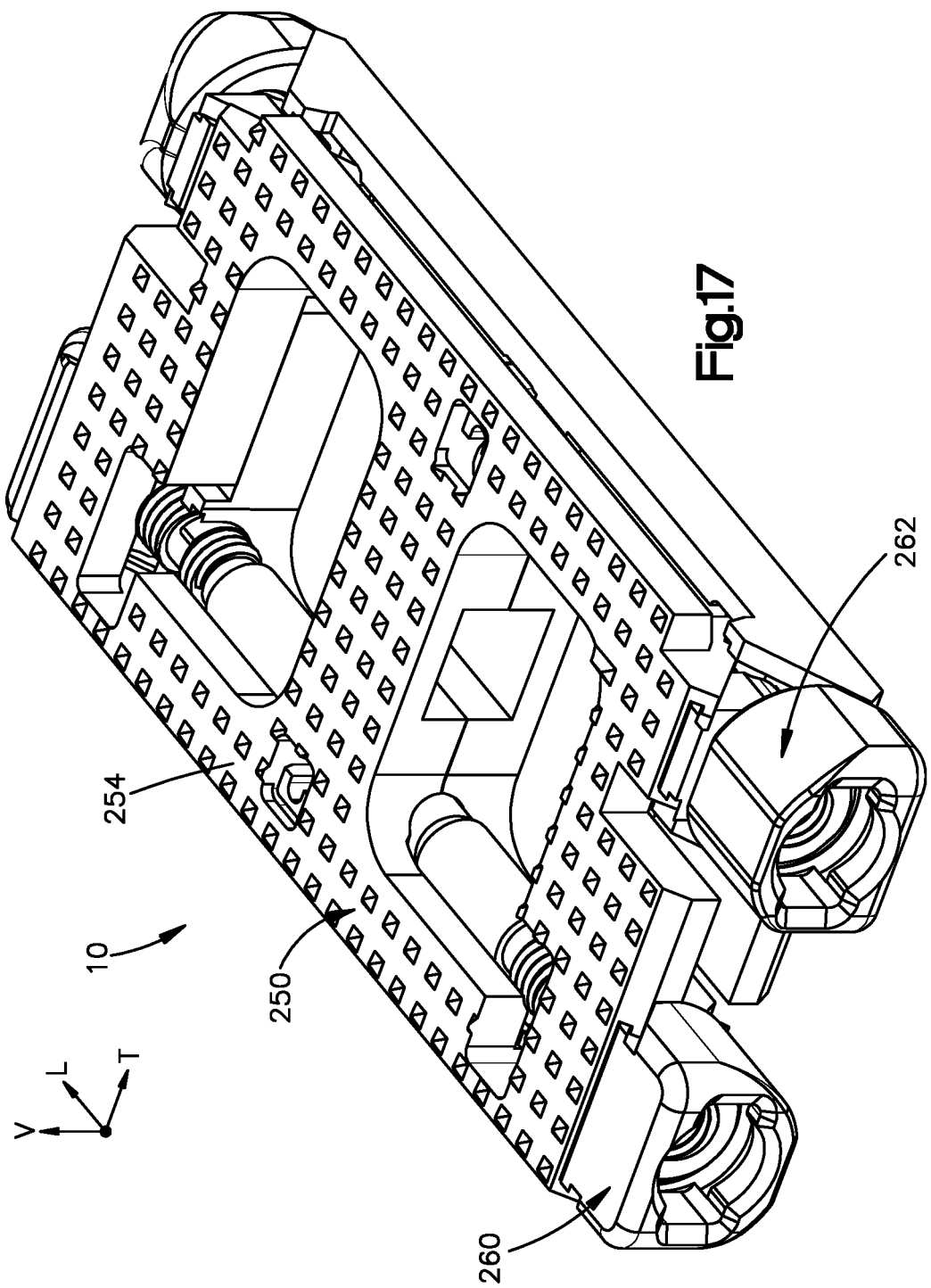

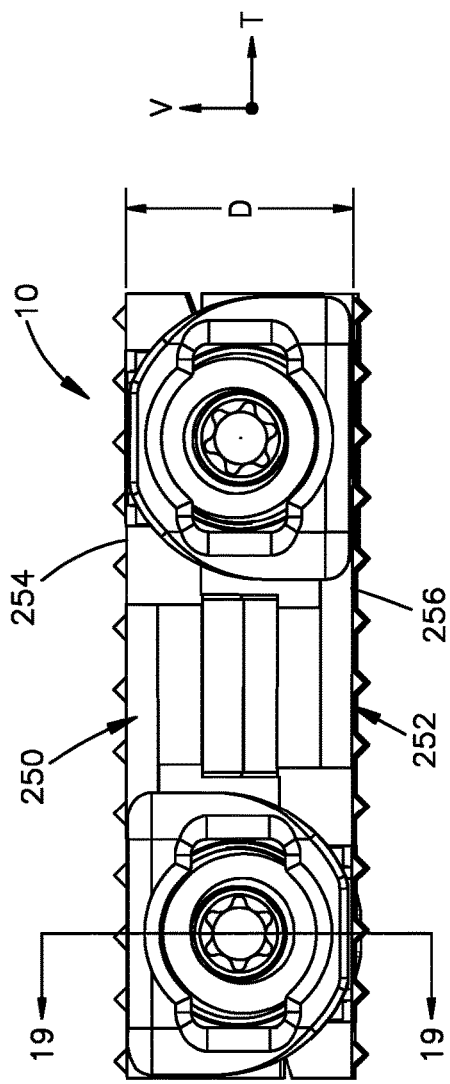
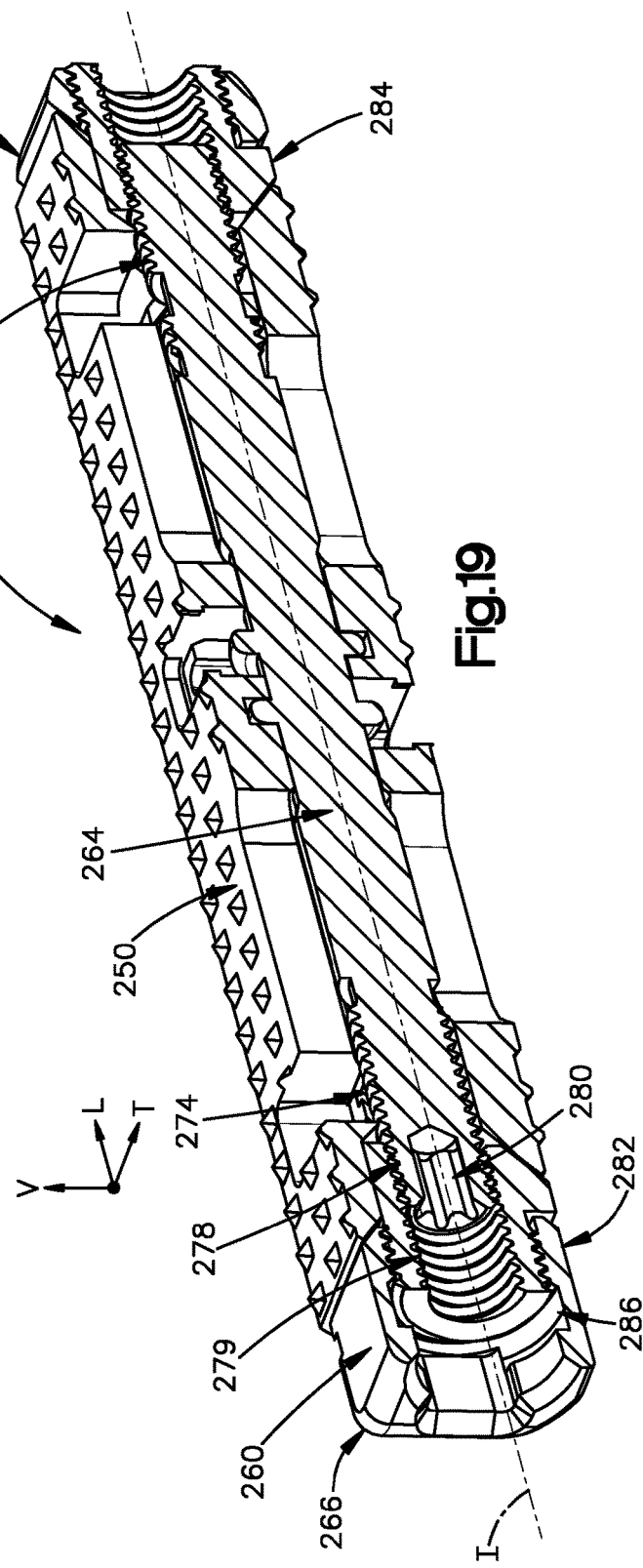

EXPANDABLE CAGE ADJUSTMENT TOOL AND METHOD

TECHNICAL FIELD

The present invention relates to expandable intervertebral implant inserters, assemblies, and associated methods and procedures for using the same.

BACKGROUND

Removal of an intervertebral disc is often desired if the disc degenerates. Spinal fusion may be used to treat such a condition and involves replacing a degenerative disc with a device such as a cage or other spacer that restores the height of the disc space and allows bone growth through the device to fuse the adjacent vertebrae. Spinal fusion attempts to restore normal spinal alignment, stabilize the spinal segment for proper fusion, create an optimal fusion environment, and allows for early active mobilization by minimizing damage to spinal vasculature, dura, and neural elements. When spinal fusion meets these objectives, healing quickens and patient function, comfort and mobility improve. Spacer devices that are impacted into the disc space and allow growth of bone from adjacent vertebral bodies through the upper and lower surfaces of the implant are known in the art. Yet there continues to be a need for devices that minimize procedural invasiveness yet stabilize the spinal segment and create an optimum space for spinal fusion.

The spacer devices can be inserted and adjusted within the disc space using an implant adjustment tool. Adjustment tools are used to adjust both expansion height and lordosis angle of the implant. For example, the adjustment tool can connect to a height adjuster on the spacer device for increasing and decreasing height. Spacer devices can include more than one height adjuster to also allow adjustment of the lordosis angle. However, there are challenges with conventional adjustment tools, such as measuring expansion of the implant, controlling both height and lordosis angle, and maintaining the connection between the adjustment tool and the spacer device, which can adversely affect the overall performance of the spacer device, and consequently, adversely affect the treatment of the spine.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

The foregoing needs are met, to a great extent, by the implant adjustment tools and methods disclosed in the present application.

According to an embodiment of the present disclosure, an adjustment tool configured to adjust an intervertebral implant is disclosed. The adjustment tool comprises a housing, a traveler member, a tether member, and a drive member. The traveler member is coupled to the housing such that rotation of the traveler relative to the housing causes linear movement of the traveler relative to the housing. The tether member has a proximal end and an opposing distal end, the proximal end being coupled to the traveler, and the distal end being configured to couple to the implant. The tether member is substantially linearly fixed to the traveler and rotatable relative to the traveler. The drive member is configured to transition between 1.) a first position in which the drive member is coupled to the tether such that rotation of the drive member causes rotation of the tether relative to the traveler, and 2.) a second position in which the drive member is coupled to the traveler such that rotation of the drive member causes rotation of the traveler relative to the housing.

According to another embodiment of the present disclosure, an adjustment tool configured to adjust an intervertebral implant is disclosed. The adjustment tool comprises a housing, first and second traveler members, first and second tether members, first and second drive members, and a gear assembly. The first traveler member is coupled to the housing such that the first traveler member is rotatable relative to the housing. The second traveler member is coupled to the housing such that the second traveler member is rotatable relative to the housing. The first tether member is coupled to the first traveler member, and the second tether member is coupled to the second traveler member. The first drive member is rotationally coupled to the first traveler member such that rotation of the first drive member causes rotation of the first traveler member and further causes linear movement of the first tether member relative to the housing. The second drive member rotationally coupled to the second traveler member such that rotation of the second drive member causes rotation of the second traveler member and further causes linear movement of the second tether member relative to the housing. The gear assembly comprises a first gear member and a second gear member. The first gear member is rotationally coupled to the first drive member such that rotation of the first drive member causes rotation of the first gear member. The second gear member is coupled to the second drive member such that the second gear member rotates independently of the second drive member. The second gear member is further rotationally coupled to the first gear member such that rotation of the second gear member causes rotation of the first gear member.

According to another embodiment of the present disclosure, an adjustment tool configured to adjust an intervertebral implant is disclosed. The adjustment tool comprises a housing, first and second traveler members, first and second tether members, first and second drive members, and a gear assembly. The first traveler member is coupled to the housing such that the first traveler member is rotatable relative to the housing. The second traveler member is coupled to the housing such that the second traveler member is rotatable relative to the housing. The first tether member is coupled to the first traveler member such that rotation of the first traveler member causes linear movement of the first tether member relative to the housing. The second tether member is coupled to the second traveler member such that rotation of the first traveler member causes linear movement of the first tether member relative to the housing.

The gear assembly comprises a first gear member and a second gear member. The first gear member is rotationally coupled to the first drive member such that rotation of the first drive member causes rotation of the first gear member. The first gear member is configured to transition between 1.) a first position in which the first gear member is rotationally coupled to the first traveler member such that rotation of the first gear member causes rotation of the first traveler member, and 2.) a second position in which the first gear member is de-coupled from the first traveler member. The second gear member is rotationally coupled to the second drive member such that rotation of the second drive member causes rotation of the second gear member. The second gear member is configured to transition between 1.) a first position in which the second gear member is rotationally coupled to the second traveler member such that rotation of the second gear member causes rotation of the second traveler member, and 2.) a second position in which the second gear member is de-coupled from the first traveler member.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 6 illustrates a first elevation view of a housing of the implant adjustment tool shown in FIG. 3;

FIG. 7 illustrates a cross-sectional view of the housing show in FIG. 6 taken along line 7-7;

FIG. 8 illustrates a first side perspective view of traveler members of the implant adjustment tool shown in FIG. 3;

FIG. 9 illustrates a second side perspective view of traveler members shown in FIG. 8;

FIG. 10 illustrates a first elevation view of traveler members of the implant adjustment tool shown in FIG. 3;

FIG. 11 illustrates a cross-sectional view of traveler members show in FIG. 10 taken along line 11-11;

FIG. 12 illustrates a first side perspective view of tether members of the implant adjustment tool shown in FIG. 3;

FIG. 13 illustrates a second side perspective view of the tether members shown in FIG. 12;

FIG. 14 illustrates a first elevation view of tether members of the implant adjustment tool shown in FIG. 3;

FIG. 15 illustrates a cross-sectional view of the tether members shown in FIG. 10 taken along line 15-15;

FIG. 17 illustrates a perspective view of an implant, according to an aspect of this disclosure;

FIG. 18 illustrates a first elevation view of the implant shown in FIG. 17;

FIG. 19 illustrates a cross-sectional view of the implant shown in FIG. 18 taken along line 19-19;

DETAILED DESCRIPTION OF ILLUSTRATIVE EMBODIMENTS

Figure 1:
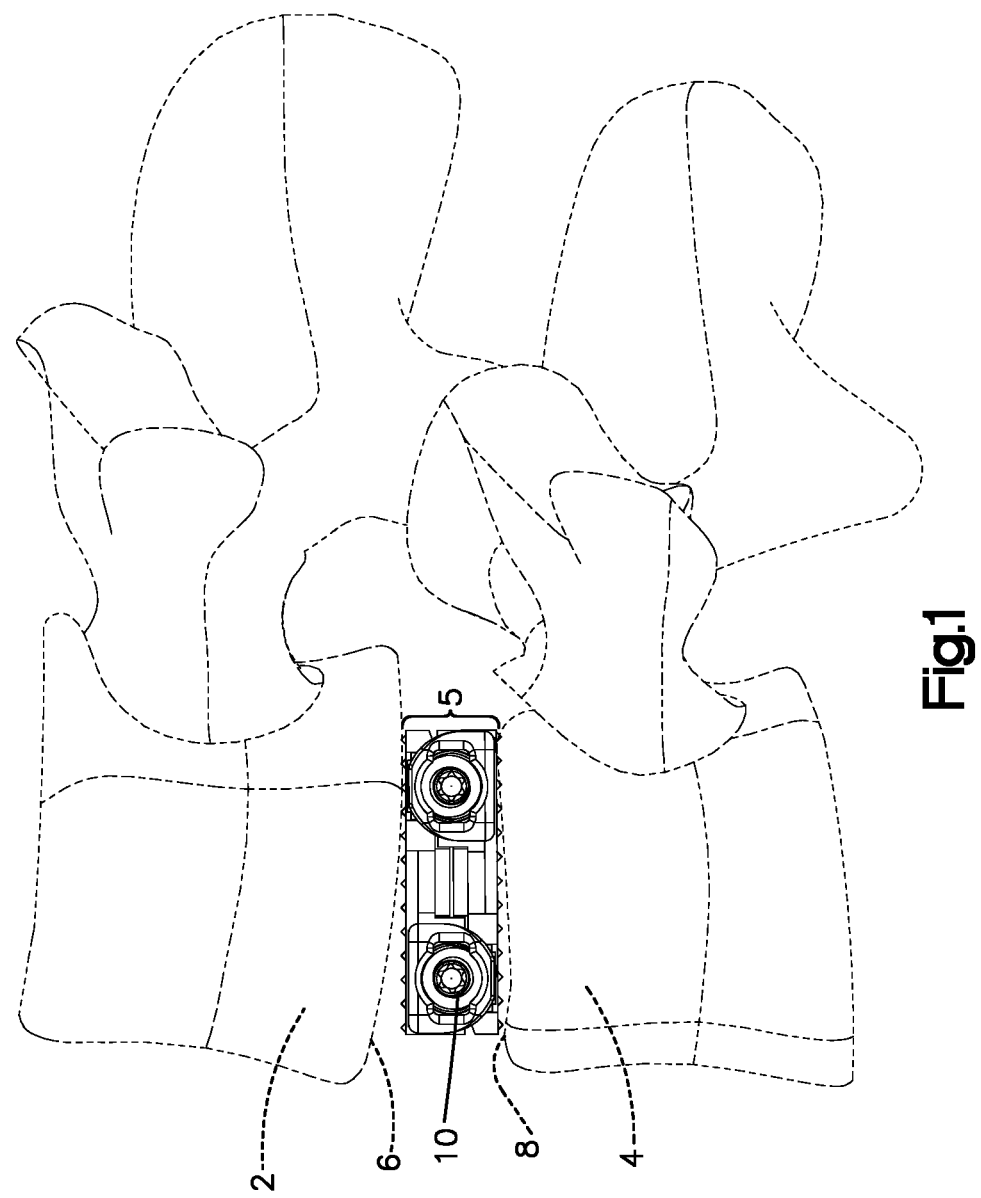
FIG. 1 is an end view of an implant positioned between adjacent vertebral bodies, according to an aspect of this disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

Certain terminology used in this description is for convenience only and is not limiting. The words "top", "bottom", "distal", "proximal", "leading", "trailing", "inner", "outer", "above", "below", "axial", "transverse", "circumferential," and "radial" designate directions in the drawings to which reference is made. The words "inner", "internal", and "interior" refer to directions towards the geometric center of the implant and/or implant adjustment tools, while the words "outer", "external", and "exterior" refer to directions away from the geometric center of the implant and/or implant adjustment tools. The words, "anterior", "posterior", "superior," "inferior," "medial," "lateral," and related words and/or phrases are used to designate various positions and orientations in the human body to which reference is made. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. The term "substantially" is intended to mean considerable in extent or largely but not necessarily wholly that which is specified. All ranges are inclusive and combinable. The terminology includes the above-listed words, derivatives thereof and words of similar import.

Referring to FIG. 1, a superior vertebral body 2 and an adjacent inferior vertebral body 4 define an intervertebral space 5 extending between the vertebral bodies 2, 4. The superior vertebral body 2 defines superior vertebral surface 6, and the adjacent inferior vertebral body 4 defines an inferior vertebral surface 8. The vertebral bodies 2 and 4 can be anatomically adjacent, or can be remaining vertebral bodies after an intermediate vertebral body has been removed from a location between the vertebral bodies 2 and 4. The intervertebral space 5 in FIG. 1 is illustrated after a discectomy, whereby the disc material has been removed or at least partially removed to prepare the intervertebral space 5 to receive an expandable intervertebral implant 10. The implant 10 is shown in a collapsed configuration, in which configuration the implant 10 can be configured for lateral insertion (i.e., along a medial-lateral trajectory) within the intervertebral space 5.

Once inserted in the intervertebral space 5, the implant 10 can be expanded in a cranial-caudal (i.e., vertical) direction, or otherwise iterated, between the collapsed configuration and a fully expanded configuration to achieve appropriate height restoration. Additionally, one of the sides of the implant 10 can be expanded vertically to a greater extent than the opposite side to achieve lordosis or kyphosis, as disclosed in more detail below. The intervertebral space 5 can be disposed anywhere along the spine as desired, including at the lumbar, thoracic, and cervical regions of the spine.

Figure 2:
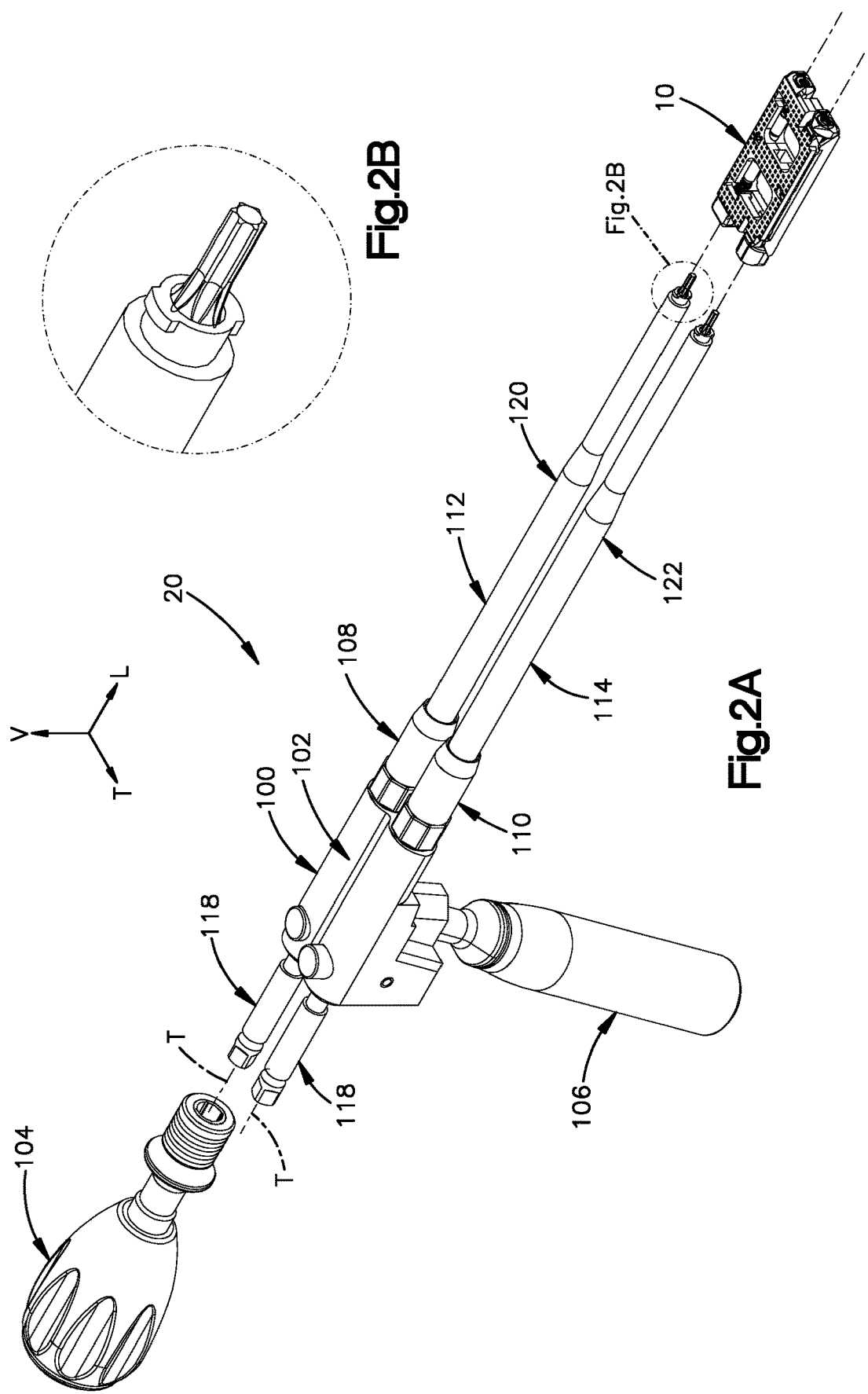
FIG. 2A illustrates a perspective view of an implant adjustment system, according to an aspect of this disclosure.
FIG. 2B illustrates a close-up view of a distal end of the implant adjustment system shown in FIG. 2A.

FIG. 2 illustrates a perspective view of an implant adjustment system 20, according to an aspect of this disclosure. The implant adjustment system 20 includes the implant 10 and an implant adjustment tool 100. The adjustment tool 100 is configured to engage and transition the implant 10 between the expanded configuration and the collapsed configuration. The adjustment tool 100 may also be configured to align and position the implant 10 within the intervertebral space 5.

The implant adjustment system 20 is described herein as extending horizontally along a longitudinal direction "L" and a transverse direction "T", and vertically along a vertical direction "V". The longitudinal direction L can be at least substantially perpendicular to each of the transverse and vertical directions T and V. The transverse direction T can be at least substantially perpendicular to each of the longitudinal and vertical directions L and V. The vertical direction V can be at least substantially perpendicular to each of the longitudinal and transverse directions L and T. Unless otherwise specified herein, the terms "longitudinal," "transverse," and "vertical" are used to describe the orthogonal directional components of various adjustment system components; however, such directional terms can be used consistently with reference to the system regardless of its actual orientation. Additionally, it should be appreciated that while the longitudinal and transverse directions L and V are illustrated as extending along and defining a horizontal plane (also referred to herein as a "longitudinal-transverse plane"), and that the vertical direction is illustrated as extending along a vertical plane (such as either a "vertical-longitudinal plane" or a "vertical-transverse plane," as respectively referred to herein), the planes that encompass the various directions may differ during use. For instance, when the implant 10 is inserted into the intervertebral space 5, the vertical direction V extends generally along the superior-inferior (or caudal-cranial) direction, the longitudinal direction L extends generally along the medial-lateral direction, and the transverse direction L extends generally along the anterior-posterior direction. Thus, the horizontal plane lies generally in the anatomical plane defined by the anterior-posterior direction and the medial-lateral direction. Accordingly, the directional terms "vertical", "longitudinal", "transverse", and "horizontal" may be used to describe the implant adjustment system 20 and its components as illustrated merely for the purposes of clarity and illustration, and such terms. With the foregoing in mind, the terms "expand" and "expansion," when used in reference to the implant adjustment system 20, refer to expansion along the vertical direction V.

Figure 3:
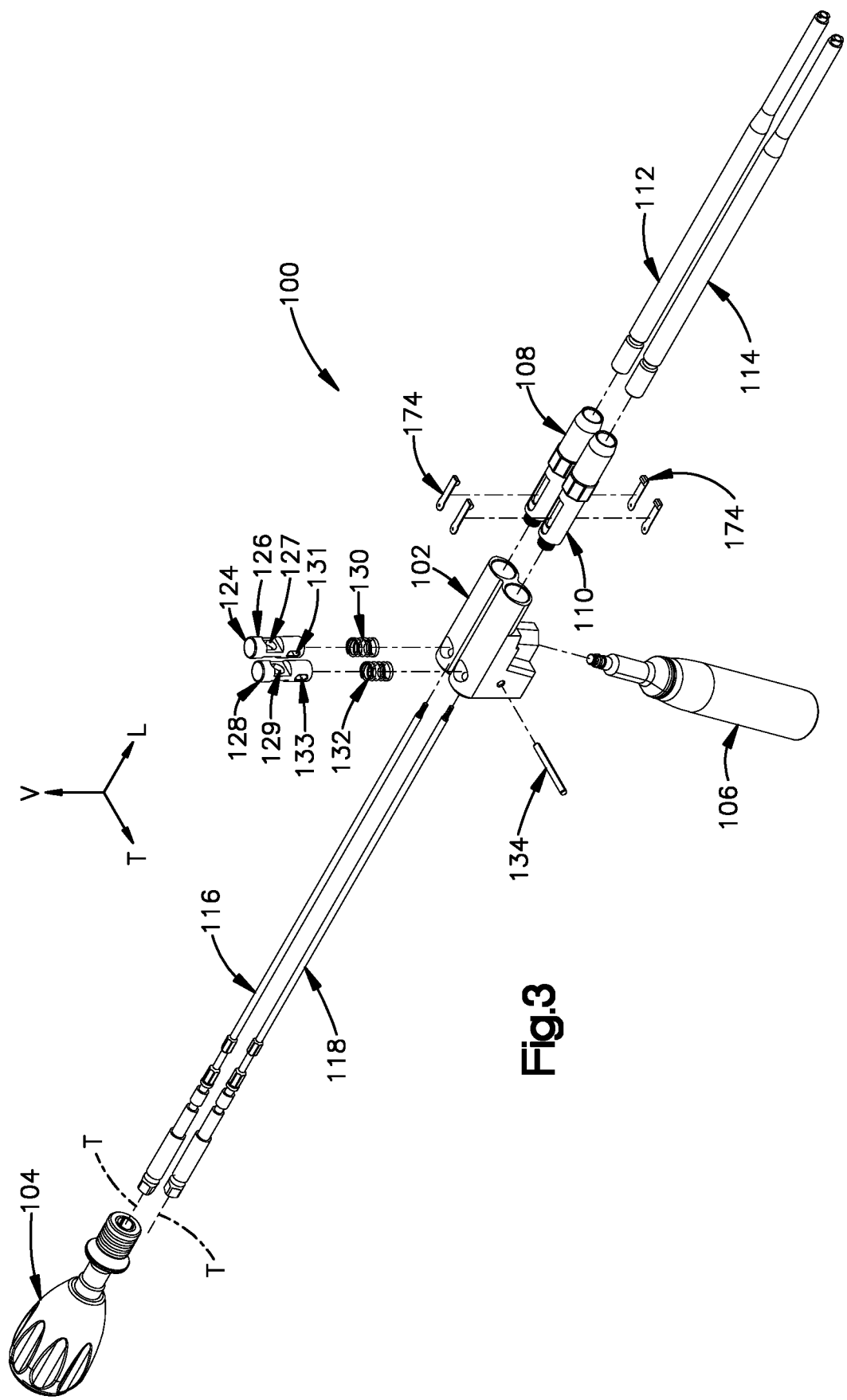
FIG. 3 illustrates an exploded perspective view of an implant adjustment tool, according to an aspect of this disclosure.

FIG. 3 illustrates an exploded view of the adjustment tool 100, according to an aspect of this disclosure. The adjustment tool 100 includes a housing 102, a handle 104, a grip member 106, a first traveler member 108, a second traveler member 110, a first tether member 112, a second tether member 114, a first drive member 116, and a second drive member 118. It will be appreciated that the adjustment tool 100 may include additional components configured to facilitate use of the adjustment tool 100. The first traveler member 108, the first tether member 112, and the first drive member 116 compose a first drive assembly 120. The second traveler member 110, the second tether member 114, and the second drive member 118 compose a second drive assembly 122.

In an assembled configuration of the adjustment tool 100, the first housing channel 136 of the housing 102, the first traveler member 108, the first tether member 112, and the first drive member 116 align along a first tool central axis T, and a second housing channel 138 of the housing 102, the second traveler member 110, the second tether member 114, and the second drive member 118 align along a second tool central axis T'. The first and second tool central axes T and T' are substantially parallel to the longitudinal direction L.

The handle 104 is configured to control the first and second drive assemblies 120 and 122. More specifically, the handle 104 is configured to removably engage and rotate each of the first and second drive members 116 and 118, as described in further detail below. The grip member 106 is coupled to the housing 102. In an aspect, the grip member 106 is threadedly coupled to a bottom of the housing 102, although the grip member 106 can be coupled to the housing 102 in another manner. The grip member 106 is configured to allow an operator (e.g. physician) to grip the implant adjustment tool 100 to align and position the implant adjustment system 20 during a surgical operation.

The adjustment tool 100 further includes a control assembly 124 coupled to the housing 102. The control assembly 124 includes a first actuator member 126, a second actuator member 128, a first resilient member 130, a second resilient member 132, and a retention member 134. The first actuator member 126 and the first resilient member 130 may further compose the first drive assembly 120, and the second actuator member 128 and the second resilient member 132 may further compose the second drive assembly 122. The control assembly 124 is configured to control movement of the first and second drive members 116 and 118 within the housing 102, as further described below.

The first and second actuator members 126 and 128 include respective first and second actuator drive channels 127 and 129, and respective first and second actuator pin channels 131 and 133. The first and second actuator drive channels 127 and 129 and the first and second actuator pin channels 131 and 133 are configured to align with other components of the adjustment tool 100, as further described below. The first actuator drive channel 127 and the first actuator pin channel 131 extend through the first actuator member 126, and the second actuator drive channel 129 and the second actuator pin channel 133 extend through the second actuator member 128. In an aspect, the first and second actuator drive channels 127 and 129 are substantially perpendicular to the first and second actuator pin channels 131 and 133. For example, in the assembled configuration of the adjustment tool 100, the first and second actuator drive channels 127 and 129 are substantially parallel to the longitudinal direction L, and the first and second actuator pin channels 131 and 133 are substantially parallel to the transverse direction T.

Figure 5:
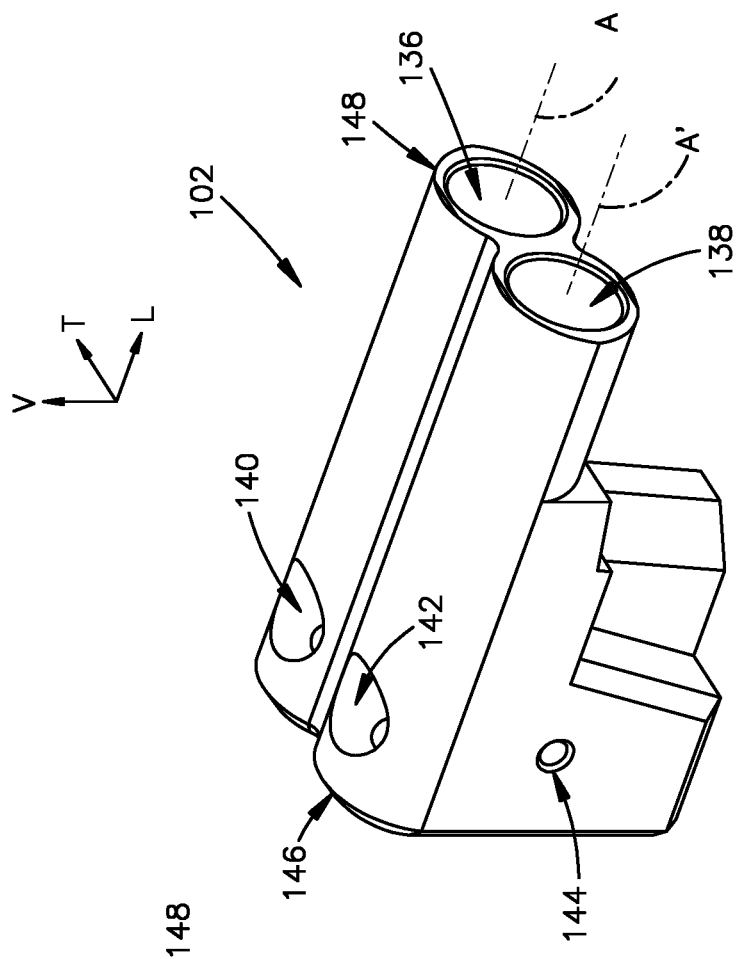
FIG. 5 illustrates a second side perspective view of the housing shown in FIG. 4.
Figure 4:
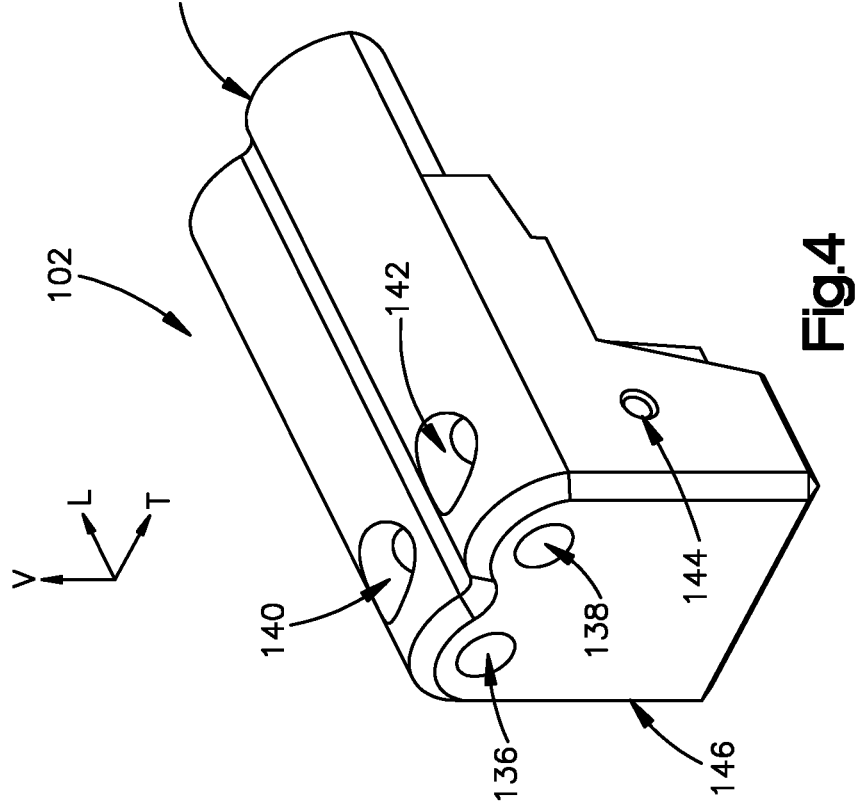
FIG. 4 illustrates a first side perspective view of a housing of the implant adjustment tool shown in FIG. 3.

FIGS. 4 and 5 illustrate a first side perspective view of the housing 102 and a second side perspective view of the housing 102, respectively, according to aspects of this disclosure. The housing 102 defines the first drive channel 136 (e.g. first housing channel), a second drive channel 138 (e.g. second housing channel), a first control channel 140, a second control channel 142, and a pin channel 144. The first and second drive channels 136 and 138 extend through the housing 102 from a distal end 146 to a proximal end 148 in the longitudinal direction L. The first and second control channels 140 and 142 extend at least partially through the housing 102 in the vertical direction V. The pin channel 144 extends at least partially through the housing 102 in the transverse direction T. The first drive channel 136 aligns with the first control channel 140 such that the first drive channel 136 intersects the first control channel 140. Similarly, the second drive channel 138 aligns with the second control channel 142 such that the second drive channel 138 intersects the second control channel 142.

The pin channel 144 aligns with both of the first and second control channels 140 and 142 such that both of the first and second control channels 140 and 142 intersect with the pin channel 144. In an aspect, the pin channel 144 may comprise a first pin channel and a second pin channel, whereby the first pin channel intersects the first control channel 140, and the second pin channel intersects the second control channel 142. The pin channel 144 is configured to receive the retention member 134 within. The retention member 134 is configured to extend through the pin channel 144 such that the retention member 134 intersects both of the first and second control channels 140 and 142. In an aspect, the adjustment tool 100 may comprise a first and a second retention member configured to be received within the first pin channel and the second pin channel, respectively, such that the first retention member intersects the first control channel 140, and the second retention member intersects the second control channel 142.

FIG. 6 illustrates a first elevation view of the housing 102, and FIG. 7 illustrates a cross-sectional view of the housing 102 taken along line 7-7 of FIG. 6, according to aspects of this disclosure. The first drive channel 136 extends about a first central housing axis A. The first central housing axis A is substantially parallel to the longitudinal direction L. The first drive channel 136 includes a proximal drive portion 137 and a distal drive portion 139. The proximal drive portion 137 extends from the proximal end 146 of the housing 102 to the distal drive portion 139. The distal drive portion 139 extends from the proximal drive portion 137 to the distal end 148 of the housing 102. A cross sectional dimension (e.g. a diameter) of the distal drive portion 139 is greater than a cross sectional dimension (e.g. a diameter) of the proximal drive portion 137, thereby defining a shoulder 150 therebetween. A distal end of the proximal drive portion 137 includes a threaded section 152. The first traveler member 108 is configured to couple to the housing 102, such that the threaded section 152 of the first drive portion 137 threadedly engages a corresponding threaded section of the first traveler member 108, and the shoulder 150 abuts against a corresponding shoulder 168 (see FIG. 8) of the first traveler member 108, as further described below. It will be appreciated that the first drive channel 136 and the second drive channel 138 can be configured substantially similarly; accordingly, the same reference numbers will be used herein with reference to corresponding components and features of the first and second drive channels 136 and 138. As such, the second drive channel 138 includes a first drive portion 137', a second drive portion 139', a shoulder 150', a threaded section 152', and a second central housing axis A'.

The first and second control channels 140 and 142 of the housing 102 are sized to receive the first and second actuator members 126 and 128 within, respectively. In an aspect, the first and second actuator members 126 and 128 are coaxial with respective central axes of the first and second control channels 140 and 142 of the housing 102. In the assembled configuration of the adjustment tool 100, the first and second actuator pin channels 131 and 133 of the first and second actuator members 126 and 128 align with the pin channel 144 of the housing 102, and the first and second actuator drive channels 127 and 129 of the first and second actuator members 126 and 128 align with the first and second drive channels 136 and 138, respectively, of the housing 102. The retention member 134 is configured to extend through the pin channel 144 and the first and second actuator pin channels 131 and 133 of the first and second actuator members 126 and 128 to substantially retain the first and second actuator members 126 and 128 at least partially within the housing 102.

FIGS. 8 and 9 illustrate a first side perspective view of the first and second traveler members 108 and 110, and a second side perspective view of the first and second traveler members 108 and 110, respectively, according to aspects of this disclosure. The first traveler member 108 extends from a proximal end 156 to a distal end 158. The first traveler member 108 includes a connection portion 160, a proximal portion 162, and a distal portion 164.

The connection portion 160 extends from the proximal end 156 to the proximal portion 162 and includes an externally threaded portion 166. The externally threaded portion 166 is configured to threadedly mate with the threaded section 152 of the first drive portion 137. A cross-sectional dimension (e.g. a diameter) of the connection portion 160 may be less than a cross-sectional dimension (e.g. a diameter) of the proximal portion 162, thereby defining the shoulder 168 therebetween. The shoulder 168 is defined on an outer surface of the first traveler member 108, and is configured to abut against the corresponding shoulder 150 of the first drive portion 137.

The proximal portion 162 extends between the connection portion 160 and the distal portion 164. The proximal portion 162 defines a first opening 170 and a second opening 172. Both of the first and second openings 170 and 172 extend through a wall of the proximal portion 162 from an exterior to a first traveler channel 180 defined within the first traveler member 108. In an aspect, there may be fewer or more openings defined by the proximal portion 162. In a further aspect, each of the openings defined by the proximal portions 162 may oppose a corresponding opening in a radial direction. With reference to FIG. 3, the first and second openings 170 and 172 are configured to receive tether retention members 174 within. Each of the tether retention members 174 may be coupled to first traveler member 108 such that at least a portion of each of the tether retention members 174 extend into the first traveler channel 180. The distal portion 164 extends from the proximal portion 162 to the distal end 158 of the first traveler member 108. It will be appreciated that the distal portion 164 may also include one or more openings configured substantially similarly to the openings defined by the proximal portion 162.

The first traveler member 108 may also include a grip portion 176 positioned between the proximal portion 162 and the distal portion 164. The grip portion 176 may be configured to facilitate gripping and/or rotating the first traveler member 108 during use. The grip portion 176 may comprise a flat shape with straight sides such as, for example, a rectangular shape, hexagonal shape, octagonal shape, or other shape to facilitate gripping, such as, for example, a protrusion, a recess, or a plurality of ridges or perforations. Alternatively, the grip portion 176 may comprise a rubber type grip or a rubber tape.

FIG. 10 illustrates a first elevation view of the first and second traveler members 108 and 110, and FIG. 11 illustrates a cross-sectional view of the first traveler member 108 taken along line 11-11 of FIG. 10, according to aspects of this disclosure. The connection portion 160, the proximal portion 162, and the distal portion 164 define the first traveler channel 180 that extends through the first traveler member 108 from the proximal end 156 to the distal end 158. The first traveler channel 180 extends about a first central traveler axis B. The first central traveler axis B is substantially parallel to the longitudinal direction L. The first traveler channel 180 is configured to receive at least a portion of the first tether member 112 within. An inner surface of the first traveler channel 180 defines a shoulder 182. In an aspect, the shoulder 182 is located at or near a proximal end of the proximal portion 162. The shoulder 182 is configured to prevent a proximal end of the first tether member 112 from translating from the first traveler channel 180 defined by the proximal portion 162 into the portion of the first traveler channel 180 defined by the connection portion 160, as further described below.

An inner surface 169 of the connection portion 160 defines a shaped structure that is configured to engage and rotationally lock to the first drive member 116, as further described below. The shaped structure corresponds to a shape of the first drive member 116 and may include, for example, a flat shape with straight sides such as, for example, a rectangular shape, hexagonal shape, octagonal shape, or other keyed type shape such as a protrusion, a recess, or a series of protrusions and/or recesses.

It will be appreciated that the first traveler member 108 and the second traveler member 110 can be configured substantially similarly; accordingly, the same reference numbers will be used herein with reference to corresponding components and features of the first and second traveler members 108 and 110. As such, the second traveler member 110 includes a connection portion 160', a proximal portion 162', a distal portion 164', a shoulder 168', an inner surface 169', first and second openings 170' and 172', a second traveler channel 180', a shoulder 182', and a second central traveler axis B'.

FIGS. 12 and 13 illustrate a first side perspective view of the first and second tether members 112 and 114, and a second side perspective view of the first and second tether members 112 and 114, respectively, according to aspects of this disclosure. The first tether member 112 extends from a proximal end 190 to a distal end 192. The first tether member 112 includes a recess 194 that extends circumferentially about an outer surface of the first tether member 112. The recess 194 is positioned toward the proximal end 190. In the assembled configuration of the adjustment tool 100, the proximal end 190 is positioned within the first traveler member 108 such that the recess 194 receives a portion of at least one of the tether retention members 174 within. The recess 194 and the corresponding tether retention member 174 are configured to substantially prevent linear movement of the first traveler member 108 relative to the first traveler member 112, while allowing rotational movement between the first traveler member 108 and the first traveler member 112.

The first tether member 112 includes a first lock member 196 positioned at the distal end 192. The first lock member 196 is configured to linearly interlock the first tether member 112 with a corresponding proximal wedge assembly 282 (see FIG. 19) on the implant 10. The first lock member 196 may comprise partial threads, a rotational snap-fit member, or other feature configured to interlock the first lock member 196 with the wedge assembly 282 (e.g. first expansion wedge) of the implant 10. The interlock between the first lock member 196 and the wedge of the implant 10 substantially linearly fixes the first lock member 196 to the wedge. The interlock between the first lock member 196 and the wedge is removable, such that the first tether member 112 can be attached and detached (e.g. locked and unlocked) from the implant 10.

FIG. 14 illustrates a first elevation view of the first and second tether members 112 and 114, and FIG. 15 illustrates a cross-sectional view of the first tether member 112 taken along line 15-15 of FIG. 14, according to aspects of this disclosure. The first tether member 112 includes an inner surface 198 that defines a first tether channel 200 that extends through the first tether member 112 from the proximal end 190 to the distal end 192. The first tether channel 200 extends about a first central tether axis C. The first central tether axis C is substantially parallel to the longitudinal direction L. The first tether channel 200 is configured to receive the first drive member 116 within, such that the first drive member 116 can extend through the first tether member 112.

The tether channel 200 includes a drive connect portion 202, a drive disconnect portion 204, and a distal portion 206. The drive connect portion 202 extends from the proximal end 190 to the drive disconnect portion 204. The inner surface 198 of the drive connect portion 202 defines a shaped structure that is configured to engage and rotationally interlock with the first drive member 116, such that rotation of the first drive member 116 causes rotation of the first tether member 112, as further described below. The shaped structure corresponds to a shape of the first drive member 116 and may include, for example, a flat shape with straight sides such as, for example, a rectangular shape, hexagonal shape, octagonal shape, or other keyed type shape such as a protrusion, a recess, or a series of protrusions and/or recesses. In an aspect, the shaped structure of the drive connect portion 202 may be substantially similar to the shaped structure of the connection portion 160 of the first traveler member 108.

The drive disconnect portion 204 extends from the drive connect portion 202 to the distal portion 206. The inner surface 198 of the drive disconnect portion 204 defines a substantially cylindrical shape that extends circumferentially about the first central tether axis C. A cross-sectional dimension (e.g. a diameter) of the drive disconnect portion 204 is at least as big as a cross-sectional dimension (e.g. a diameter) of the drive connect portion 202. The distal portion 206 extends from the drive disconnect portion 204 to the distal end 192 of the first tether member 112. The inner surface 198 of the distal portion 206 defines a substantially cylindrical shape that extends circumferentially about the first central tether axis C. A cross-sectional dimension (e.g. a diameter) of the distal portion 206 is smaller than the cross-sectional dimension of the drive disconnect portion 204, thereby forming a shoulder 208 therebetween.

It will be appreciated that the first tether member 112 and the second tether member 114 can be configured substantially similarly; accordingly, the same reference numbers will be used herein with reference to corresponding components and features of the first and second tether members 112 and 114. As such, the second tether member 114 includes a recess 194', a second lock member 196', an inner surface 198', a second tether channel 200', a drive connect portion 202', a drive disconnect portion 204', a distal portion 206', a shoulder 208', and a second central tether axis C'.

Figure 16:
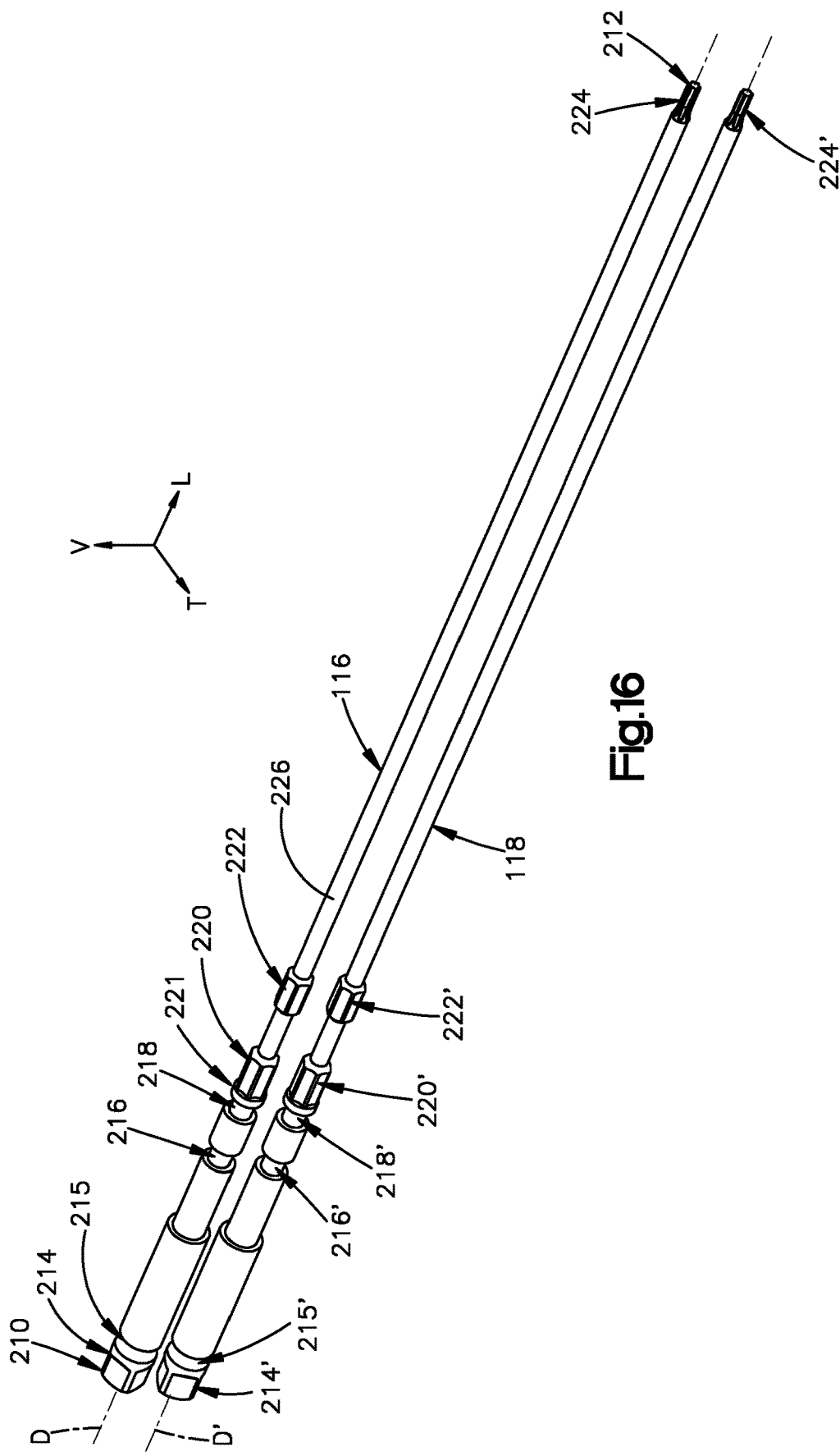
FIG. 16 illustrates a perspective view of drive members of the implant adjustment tool shown in FIG. 3.

FIG. 16 illustrates a perspective view of the first and second drive members 116 and 118, according to an aspect of this disclosure. The first drive member 116 extends from a proximal end 210 to a distal end 212 along a first central drive axis D. The first drive member 116 includes a first head 214, a first handle lock recess 215, a first traveler lock recess 216, a first tether lock recess 218, a first traveler drive member 220, a first tether drive member 222, and a first bit 224. The first head 214 can define a hexagonal or other alternatively shaped structure that can be engaged by a driving instruction (e.g. handle 104) to rotate the first drive member 116. The shaped structure of the first head 214 can be defined either by an inner surface or an outer surface. The handle 104 includes a corresponding shaped structure to engage the first head 214. The first handle lock recess 215 is configured to receive a linear lock component (not shown) from the handle 104, to removably lock the first drive member 116 to the handle 104 during use. The linear lock component can include, for example, a ball bearing or other projection. Both of the first head 214 and the first handle lock recess 215 are configured to be received within a channel (not labeled) of the handle 104.

The first traveler lock recess 216 and the first tether lock recess 218 are defined by an outer surface 226 of the first drive member 116. In an aspect, the first tether lock recess 218 is located distally from the first traveler lock recess 216. The first traveler lock recess 216 and the first tether lock recess 218 are configured to engage the control assembly 124 to control the linear movement of the first drive member 116, as further described below.

The first traveler drive member 220 and the first tether drive member 222 extend radially outward from the outer surface 226 of the first drive member 116. The first tether drive member 222 is located distally from the first traveler drive member 220. The first traveler drive member 220 is configured to engage the inner surface 169 of the first traveler member 108. The first traveler drive member 220 defines a shaped structure that corresponds to the shaped structure of the inner surface 169, such that when the first traveler drive member 220 engages the inner surface 169, the first drive member 116 is rotationally locked to the first traveler member 108. The first traveler drive member 220 is configured to transition between an engaged position, in which the first traveler drive member 220 is positioned within the first traveler channel 180 defined by the inner surface 169, and a disengaged position, in which the first traveler drive member 220 is positioned externally from the first traveler channel 180 defined by the inner surface 169. In an aspect, the first traveler drive member 220 includes a ledge 221, located at a proximal end of the first traveler drive member 220, that extends radially outward from the first traveler drive member 220. The ledge 221 has a cross-section dimension that is greater than a cross-sectional dimension of the inner surface 169, which substantially prevents the first traveler drive member 220 from translating into the first traveler channel 180 defined by the proximal portion 162 and the distal portion 164 of the first traveler member 108.

The first tether drive member 222 is configured to engage the drive connect portion 202 of the first tether member 112. The first tether drive member 222 defines a shaped structure that corresponds to the shaped structure of the inner surface 198 of the drive connect portion 202, such that when the first tether drive member 222 engages the inner surface 198 of the drive connect portion 202, the first drive member 116 is rotationally locked to the first tether member 112. The first tether drive member 222 is configured to transition between an engaged position, in which the first tether drive member 222 is positioned within the drive connect portion 202 of the first tether member 112, and a disengaged position, in which the first tether drive member 222 is positioned externally from the drive connect portion 202. In an aspect, in the disengaged position of the first tether drive member 222, the first tether drive member 222 is positioned within the disconnect portion 204 of the first tether member 112. In the disengaged position of the first tether drive member 222, the first drive member 116 is rotationally disconnected from the first tether member 112 such that the first tether drive member 222 is free to rotate within the disconnect portion 204 of the first tether member 112.

The first bit 224 is configured to engage the implant 10 and drive an actuation assembly as further described below. The first bit 224 can define a hex profile configured to engage a corresponding hex profile of the actuation assembly of the implant 10.

It will be appreciated that the first drive member 116 and the second drive member 118 can be configured substantially similarly; accordingly, the same reference numbers will be used herein with reference to corresponding components and features of the first and second drive members 116 and 118. As such, the second drive member 118 includes a second head 214', a second handle lock recess 215', a second traveler lock recess 216', a second tether lock recess 218', a second traveler drive member 220', a second tether drive member 222', and a second bit 224'.

FIGS. 17-19 illustrate a perspective view of the implant 10, a first elevation view of the implant 10, and a cross-sectional view of the implant 10 taken along line 19-19 of FIG. 18, respectively, according to aspects of this disclosure. The implant 10 can include a first or inferior plate 250 and a second or superior plate 252 spaced from each other along the vertical direction V. The inferior and superior plates 250 and 252 may be referred to as "endplates." The inferior plate 250 can define a first or inferior bone-contacting surface 254 on an exterior thereof. The superior plate 252 can define a second or superior bone-contacting surface 256 on an exterior thereof. The superior bone-contacting surface 256 can face the superior vertebral surface 6 of the superior vertebra 2 and the inferior bone-contacting surface 254 can face the inferior vertebral surface 8 of the inferior vertebral body 4. The inferior and superior bone-contacting surfaces 254 and 256 can each be substantially planar; however, in other embodiments, each bone-contacting surface 254 and 256 can be at least partially convex, for example, and can at least partially define a texture (not shown), such as spikes, ridges, cones, barbs, indentations, or knurls, which are configured to engage the respective vertebral bodies 2, 4 when the implant 10 is inserted into the intervertebral space 5.

When the implant 10 is in the collapsed configuration, the inferior and superior bone-contacting surfaces 254 and 256 can be spaced from one another by a distance D in the range of about 5 mm and about 20 mm along the vertical direction V, by way of non-limiting example, although other sizes are within the scope of the present disclosure. Additionally, when the implant 10 is in the collapsed configuration, the inferior and superior bone-contacting surfaces 254 and 256 can be parallel with one another with respect to both the transverse direction T, and thus can have a neutral (i.e., neither lordotic or kyphotic) collapsed profile. As used herein, the terms "lordosis", "kyphosis", and their respective derivatives can be used interchangeably, with each term referring to any configuration of the implant 10 wherein the inferior and superior bone-contacting surfaces 254 and 256 are angled with respect to each other in the vertical-transverse plane.

The implant 10 further includes a first or anterior actuation assembly 260 and a second actuation assembly 262, each configured to convert a rotational input force into linear expansion forces along the vertical direction V. The first and second actuation assemblies 260 and 262 can be driven so as to provide uniform or non-uniform expansion or contraction of the implant 10 along the vertical direction V, as desired by a physician. For example, either of the actuation assemblies 260 and 262 can be driven independently of the other. When driven independently, the first and second actuation assemblies 260 and 262 can expand anterior and posterior portions of the implant 10 to different expanded heights along the vertical direction V, providing the implant 10 with a lordotic profile in the intervertebral space 5. Thus, the implant 10 allows vertical expansion within the intervertebral space and adjustment of the lordotic angle of the implant 10 independently of one another.

The first and second actuation assemblies 260 and 262 can be configured substantially similarly; accordingly, the same reference numbers will be used herein with reference to the corresponding components and features of the actuation assemblies 260 and 262. The description provided below is with respect to the first actuation assembly 260, however, it will be appreciated that the description may apply to the second actuation assembly 262 and/or any other actuation assembly composing the implant 10.

The first actuation assembly 260 includes a first actuator 264, such as a first drive shaft, as shown in FIG. 19. The first drive shaft 264 defines a first central shaft axis I that extends along the longitudinal direction L, and can also define a proximal end 266 and a distal end 268 spaced from one another along the first central shaft axis I. The first drive shaft 264 can include one or more threaded portions 270 and 272 configured to transmit one or more linear drive forces along the longitudinal direction L. For example, the drive shaft 264 can include a first or proximal threaded portion 274 and a second or distal threaded portion 276 spaced distally from the proximal threaded portion 274 in the longitudinal direction L along the first central shaft axis I. The threading of the proximal and distal threaded portions 274 and 276 can have different thread qualities. For example, in the illustrated embodiment, the proximal threaded portion 274 defines a thread pattern that is oriented in a direction opposite that of the distal threaded portion 276. In this manner, upon rotation of the first drive shaft 264, the proximal threaded portion 274 can provide a first linear drive force, the distal threaded portion 276 can provide a second linear drive force, and the first and second linear drive forces can be opposite one another.

A head 278 is located on the proximal end 266 of the first shaft 264. The head 278 can be monolithic with the first drive shaft 264 or can be a separate component, such as a nut that is coupled to the proximal end 266. The head 278 defines a socket aperture 280 extending from the proximal end 266 toward the distal end 268. The socket aperture 280 can define a hex socket, as depicted, although other socket configurations can be employed for connection to the first bit 224 of the first drive member 116.

The first actuation assembly 260 can include one or more expansion assemblies (also referred to as "wedge assemblies") that expand along the vertical direction V. For example, the proximal wedge assembly 282 can be engaged with the proximal threaded portion 274 of the drive shaft 264 and a distal wedge assembly 284 can be engaged with the distal threaded portion 276 of the drive shaft 264. The proximal and distal wedge assemblies 282 and 284 are connected to the inferior and superior plates 250 and 252 such that movement of the proximal and distal wedge assemblies 282 and 284 along the drive shaft 264 cause the inferior and superior plates 250 and 252 to expand and contract in the vertical direction V. The proximal and distal wedge assemblies 282 and 284 can be configured substantially similarly, or can include variations. The proximal and distal wedge assemblies 282 and 284 can include subassemblies that include, for example, one or more wedge assembly components.

Rotation of the drive shaft 264 about the first central shaft axis I causes the proximal and distal wedge assemblies 282 and 284 to move linearly along the first central shaft axis I. For example, rotation of the drive shaft 264 about the first central shaft axis I in a first rotational direction can cause the proximal wedge assembly 282 to move along the shaft 264 toward the distal end 268 of the implant, and can cause the distal wedge assembly 284 to move along the shaft 264 toward the proximal end 266 of the implant 10. Movement of the proximal wedge assembly 282 distally and movement of the distal wedge assembly 284 proximally causes the inferior plate 250 to move upward in the vertical direction V and causes the superior plat 252 to move in an opposing downward vertical direction. Similarly, rotation of the drive shaft 264 about the first central shaft axis I in a second rotational direction, opposite the first rotational direction, can cause the proximal wedge assembly 282 to move along the shaft 264 away from the distal end 268 of the implant 10, and can cause the distal wedge assembly 284 to move along the shaft 264 away from the proximal end 266 of the implant 10. Movement of the proximal wedge assembly 282 proximally and movement of the distal wedge assembly 284 distally causes the inferior plate 250 to move in a downward vertical direction and causes the superior plat 252 to move in the opposing upward vertical direction V.

The proximal wedge assembly 282 includes a wedge lock member 286 that can be defined by an inner surface of the proximal wedge assembly 282. The wedge lock member 286 is configured to interlock with the lock member 196 first tether member 116. The interlock between the wedge lock member 286 and the lock member 196 substantially linearly fixes the first tether member to the proximal wedge assembly 282. The wedge lock element 286 can include, for example, a projection, a recess, a threaded portion, or other corresponding lock element configured to interlock with the lock member 196.

With reference to FIGS. 3-10, the adjustment tool 100 can be assembled by inserting the tether retention members 174 into the first and second openings 170 and 172 of the first traveler member 108 and the first and second openings 170' and 172' of the second traveler member 110. The first and second traveler members 108 and 110 can be inserted into the first and second drive channels 136 and 138 of the housing 102. The connection portion 160 of the first traveler member 108 can be threadedly coupled to the threaded section 152 of the first drive channel 136. Similarly, the connection portion 160' of the second traveler member 110 can be threadedly coupled to the threaded section 152' of the second drive channel 138. The first and second traveler members 108 and 110 can be inserted into the respective first and second drive channels 136 and 138 until the 168 and 168' of the respective first and second traveler members 108 and 110 abut against respective shoulders 150 and 150' of the housing 102. After the first and second traveler members 108 and 110 are positioned within the respective first and second drive channels 136 and 138, the tether retention members 174 are substantially secured within the first and second openings 170, 172, 170', and 172' of the first and second traveler members 108 and 110. The first central traveler axis B of the first traveler member 108 coaxially aligns with the first central housing axis A, and the second central traveler axis B' of the second traveler member 110 coaxially aligns with the second central housing axis A'.

With reference to FIGS. 3 and 8-15, after the first and second traveler members 108 and 110 are positioned within the respective first and second drive channels 136 and 138, the first and second tether members 112 and 114 can be inserted into the first and second traveler channels 180 and 180' of the first and second drive members 108 and 110, respectively. The proximal ends 190 and 190' of the first and second tether members 112 and 114 can be inserted into the proximal portions 162 and 162' of the first and second drive members 108 and 110, respectively, such that at least a portion of the tether retention members 174 extend into the recesses 194 and 194' of the first and second tether members 112 and 114. The tether retention members 174 form a type of snap-fit connection between the first and second tether members 112 and 114 and the respective first and second traveler members 108 and 110. After the first and second tether members 112 and 114 are positioned within the respective first and second traveler members 108 and 110, the first central tether axis C of the first tether member 112 coaxially aligns with the first central traveler axis B of the first traveler member 108, and the second central tether axis C' of the second tether member 114 coaxially aligns with the second central traveler axis B' of the second traveler member 110.

The connection between the first and second tether members 112 and 114 and the respective first and second traveler members 108 and 110 is such that the first and second tether members 112 and 114 are substantially linearly fixed relative to the respective first and second traveler members 108 and 110. The connection between the first and second tether members 112 and 114 and the respective first and second traveler members 108 and 110 also allows rotation of the first and second tether members 112 and 114 relative to the respective first and second traveler members 108 and 110. In an aspect, the first and second tether members 112 and 114 can be removed from the respective first and second traveler members 108 and 110 by applying a force to the first and second traveler members 108 and 110 in the longitudinal direction that overcomes a force applied by the tether retention members 174 to the first and second traveler members 108 and 110, thereby removing the tether retention members 174 from the recesses 194 and 194' of the first and second traveler members 108 and 110.

Either before or after the assembly of the housing 102, the first and second traveler members 108 and 110, and the first and second tether members 112 and 114, the control assembly 124 are coupled to the housing 102. The first and second resilient members 130 and 132 are inserted into the first and second control channels 140 and 142, respectively, of the housing 102. Following the insertion of the resilient members, the first and second actuator members 126 and 128 are inserted into the first and second control channels 140 and 142, respectively, of the housing 102. During insertion of the first and second actuator members 126 and 128, the first and second actuator pin channels 131 and 133 are aligned with the pin channel 144 of the housing 102, and the pin 134 is inserted through the first and second actuator pin channels and the pin channel 144, thereby substantially securing the first and second actuator members 126 and 128 and the first and second resilient members 130 and 132 at least partially within the housing 102.

After the control assembly 124 is coupled to the housing 102, the first and second drive members 116 and 118 are inserted into the respective first and second drive channels 136 and 138 through the proximal end 146 end of the housing 102, and through the respective first and second actuator drive channels 127 and 129, first and second traveler channels 180 and 180', and first and second tether channels 200 and 200'. The first and second heads 214 and 214' of the first and second drive members 116 and 118, respectively, are located external from the housing 102 at the proximal end 146. The first and second bits 224 and 224' of the first and second drive members 116 and 118, respectively, transition between positions within the respective first and second tether channels 200 and 200' and positions external to the respective first and second tether channels 200 and 200', as described in further detail below.

Figure 20:
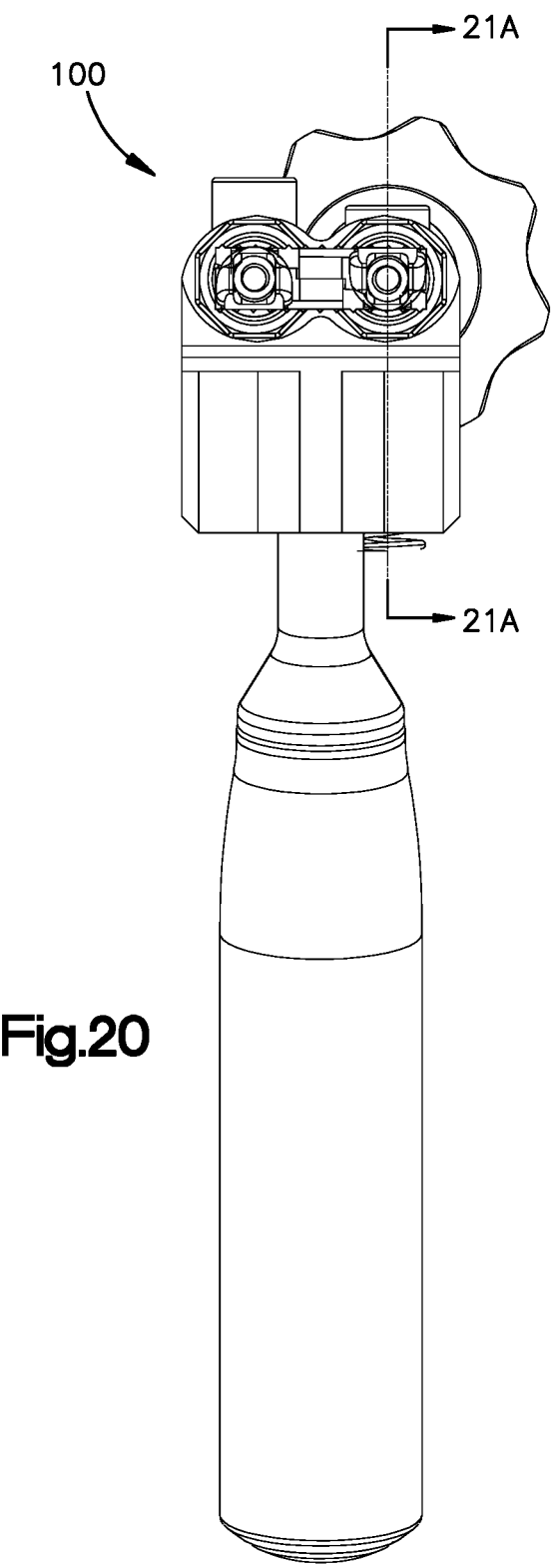
FIG. 20 illustrates a first side elevation view of the adjustment tool shown in FIG. 3.
Figure 21A:
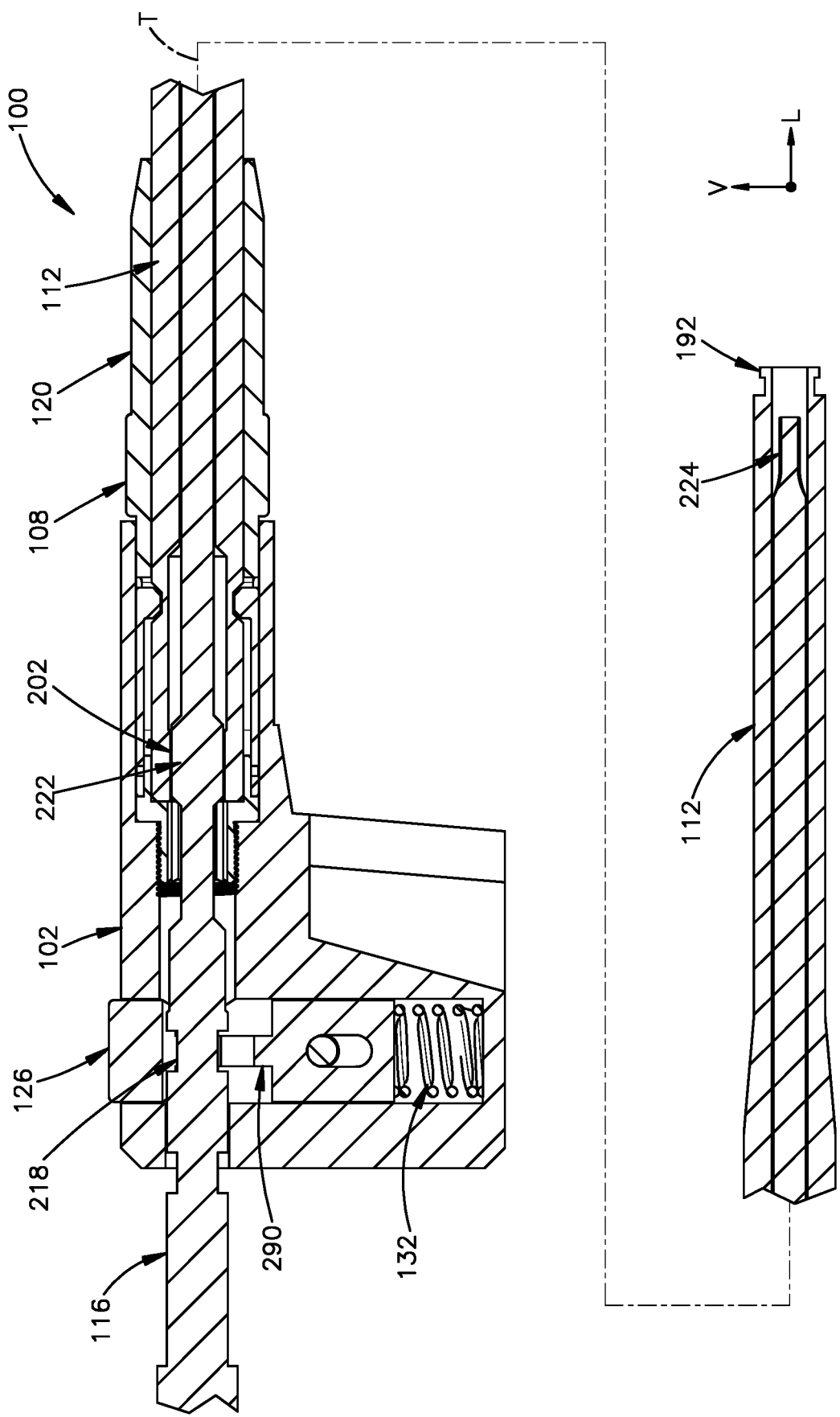
FIG. 21A illustrates a cross-sectional view of the adjustment tool shown in FIG. 20 taken along line 21-21 showing a first position of the adjustment tool.
Figure 21B:
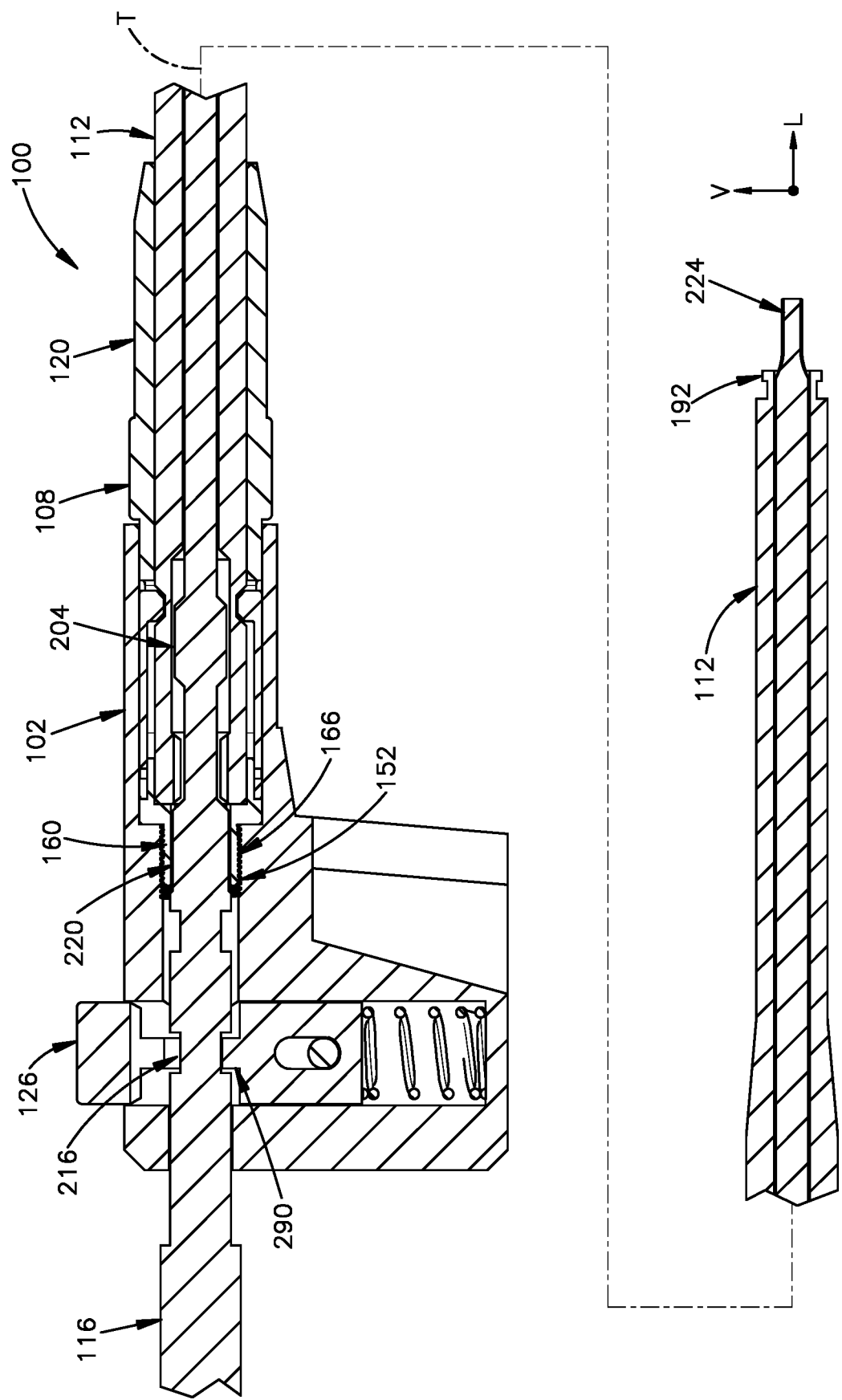
FIG. 21B illustrates a cross-sectional view of the adjustment tool shown in FIG. 20 taken along line 21-21 showing a second position of the adjustment tool.

FIG. 20 illustrates a side elevation view of the adjustment tool 100, according to an aspect of this disclosure. FIG. 21A illustrates a cross-sectional view of the adjustment tool 100 taken along line 21-21 of FIG. 20 showing a first position of the first drive member 116. FIG. 21B illustrates a cross-sectional view of the adjustment tool 100 taken along line 21-21 of FIG. 20 showing a second position of the first drive member 116. The description provided below regarding the control of the adjustment tool 100 is with respect to the first drive assembly 120, however, it will be appreciated that the description may apply to the second drive assembly 122 and/or any other drive assembly composing the adjustment tool 100.

The first drive member 116 is configured to transition between a first position and a second position. In the first position (e.g. FIG. 21A) of the first drive member 116, the first tether drive member 222 of the first drive member 116 is coupled to the drive connect portion 202 of the first tether member 112. The coupling between the first tether drive member 222 and the drive connect portion 202 substantially rotationally fixes the first drive member 116 to the first tether member 112 such that rotation of the first drive member 116 causes rotation of the first tether member 112. In the first position, both of the first drive member 116 and the first tether member 112 are rotatable relative to the first traveler member 108. The first bit 224 is positioned within the distal portion 206 of the tether channel 200.

The first drive member 116 is substantially retained in the first position by the first actuator member 126 of the control assembly 124. For example, in the first position of the first drive member 116, a portion of the first actuator member 126 extends into the first tether lock recess 218 of the first drive member 116 (e.g. locked position of the first actuator member 126), thereby coupling the first actuator member 126 to the first drive member 116 and substantially preventing linear movement of the first drive member 116 within the housing 102 along first tool central axis T. When the first actuator member 126 is coupled to the first drive member 116, the first drive member 116 is free rotate about the first tool central axis T within the housing 102. The portion of the first actuator member 126 that extends into the first tether lock recess 218 may include a projection 290, or other element configured to extend into the first tether lock recess 218. The first actuator member 126 is biased toward the locked position due to a force applied by the resilient member 132 positioned within the first control channel 140 of the housing 102.

In the second position (e.g. FIG. 21B) of the first drive member 116, the first tether drive member 222 of the first drive member 116 is positioned within the disconnect portion 204 of the first tether member 112, and first traveler drive member 220 is coupled to connection portion 160 of the first traveler member 108. The coupling between the first traveler drive member 220 and the connection portion 160 substantially rotationally fixes the first drive member 116 to the first traveler member 108 such that rotation of the first drive member 116 causes rotation of the first traveler member 108. Rotation of the first traveler member 108 within the housing 102 causes the first traveler member 108 to translate linearly in the longitudinal direction L due to the threaded connection between the externally threaded portion 166 of the first traveler member 108 and the threaded section 152 of the housing 102. Translation of the first traveler member 108 in the longitudinal direction causes the first tether member 112 to translate linearly in the longitudinal direction L due to the coupling (e.g. the tether retention members 174) between the first traveler member 108 and the first tether member 112. In the second position, both of the first drive member 116 and the first traveler member 108 are rotatable relative to the first tether member 112. The first bit 224 is positioned externally from the distal portion 206 of the tether channel 200 through the distal end 192. In an aspect, the first tether member 112 can be rotated manually by a user. For example, the first tether member 112 can be inserted into the implant 10 and manually rotated to lock the first tether member 112 to the implant 10.

The first drive member 116 is substantially retained in the second position by the first actuator member 126 of the control assembly 124. For example, in the second position of the first drive member 116, the projection 290 of the first actuator member 126 extends into the first traveler lock recess 216 of the first drive member 116 (e.g. locked position of the first actuator member 126), thereby coupling the first actuator member 126 to the first drive member 116 and substantially preventing linear movement of the first drive member 116 within the housing 102 along first tool central axis T. When the first actuator member 126 is coupled to the first drive member 116 in the second position, the first drive member 116 is free rotate about the first tool central axis T within the housing 102.

To transition the first drive member 116 between the first position and the second position, the first actuator member 126 can be transitioned from the locked position to an unlocked position. To transition the first actuator member 126 to the unlocked position, a force can be applied to the first actuator member 126 in a downward direction opposite the vertical direction V that overcomes the biasing force provided by the resilient member 132. FIG. 21A shows the first actuator member 126 in the unlocked position, and FIG. 21B shows the first actuator member 126 in the locked position.

Figure 22:
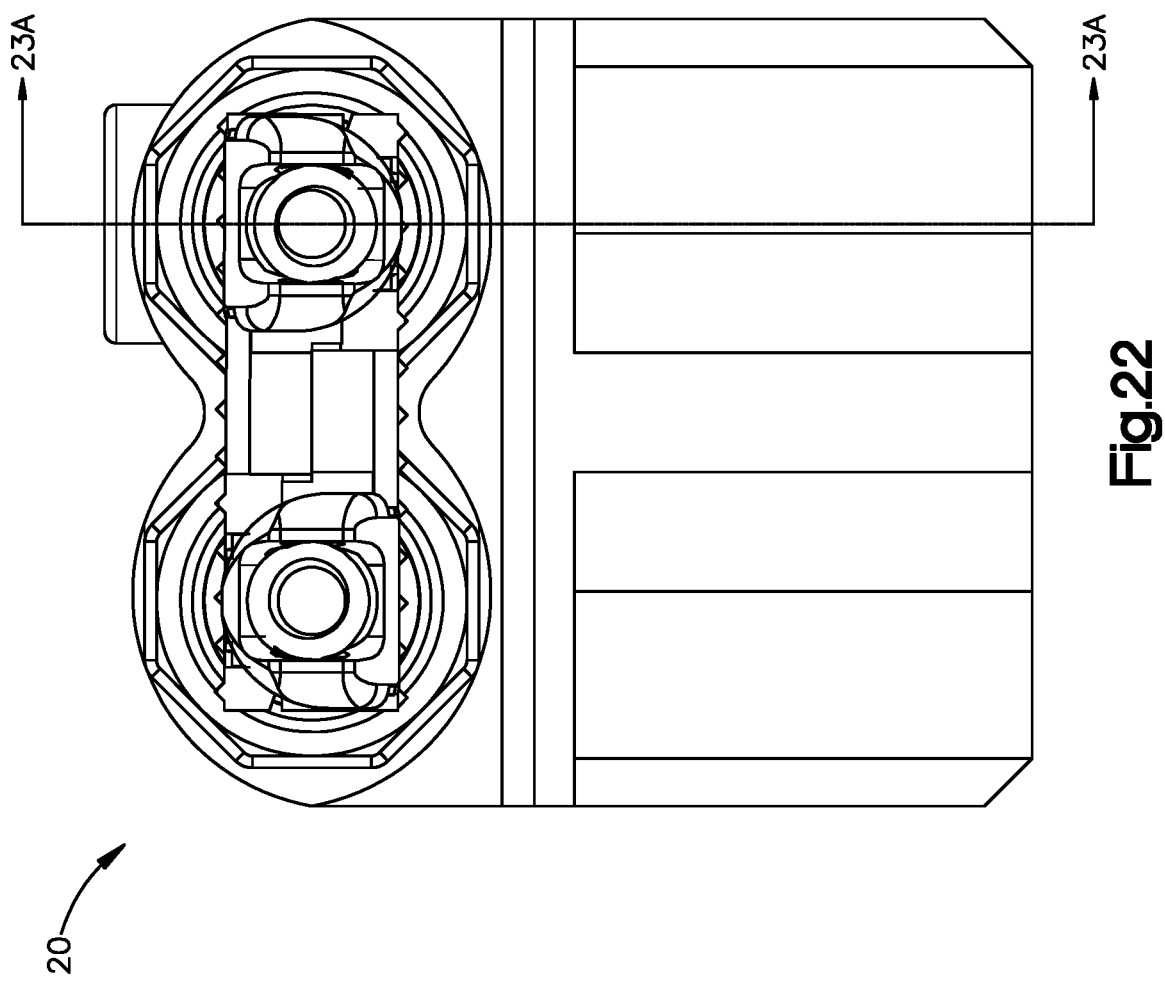
FIG. 22 illustrates a side elevation view of the implant adjustment system shown in FIG. 2.
Figure 23A:
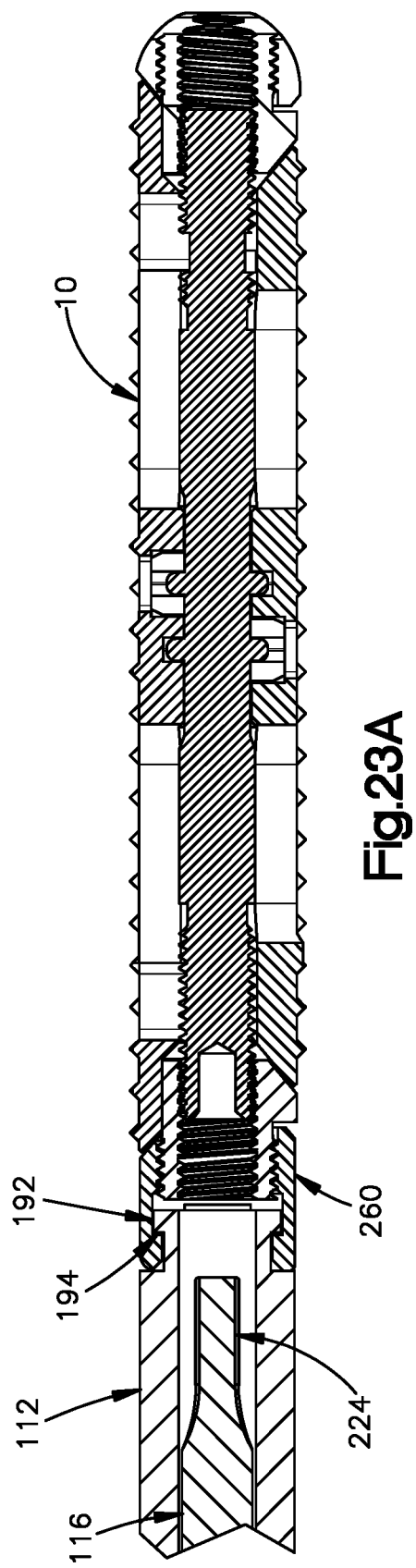
FIG. 23A illustrates a cross-sectional view of the implant adjustment system shown in FIG. 22 taken along line 23-23 showing a first position of the adjustment tool.
Figure 23B:
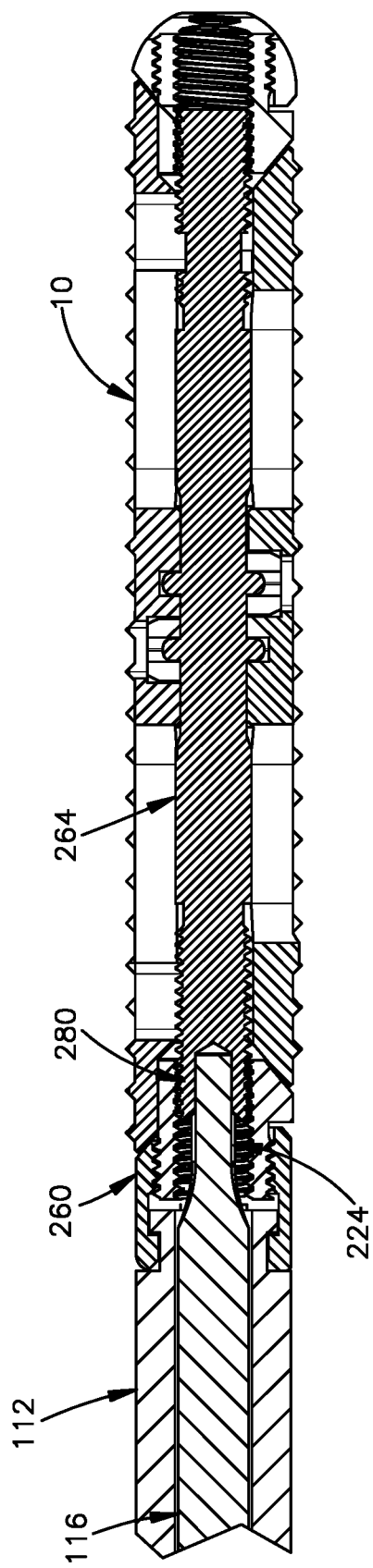
FIG. 23B illustrates a cross-sectional view of the implant adjustment system shown in FIG. 22 taken along line 23-23 showing a second position of the adjustment tool.

The adjustment tool 100 engages and transitions the implant 10 between the expanded configuration and the collapsed configuration. FIG. 22 illustrates a side elevation view of the implant adjustment system 20, according to an aspect of this disclosure. FIG. 23A illustrates a cross-sectional view of the implant adjustment system 20 taken along line 23-23 of FIG. 22 with the first drive member 116 in the first position, and FIG. 23B illustrates a cross-sectional view of the implant adjustment system 20 taken along line 23-23 of FIG. 22 with the first drive member 116 in the second position. The adjustment tool 100 is configured to engage the implant 10 by coupling the distal end 192 of the tether member 112 to the first actuation assembly 260 of the implant 10. For example, the lock member 196 at the distal end 192 of the tether member 112 is coupled to the wedge lock member 286 of the proximal wedge assembly 282. The coupling between the tether member 112 and the implant 10 can be a twist-type lock, whereby the tether member 112 is rotated relative to first actuation assembly 260 to couple the lock member 196 to the wedge lock member 286. The coupling between the first tether member 112 and the implant 10 substantially linearly fixes the first tether member 112 to the implant 10. The coupling between the first tether member 112 and the implant 10 aligns the first tool central axis T of the adjustment tool 100 with the first central shaft axis I of the implant 10.

After the first tether member 112 is coupled to the implant 10, the first drive member 116 can be transitioned from the first position to the second position. In the second position, the first bit 224 of the first drive member 116 is positioned within the socket aperture 280 of the first actuation assembly 260 of the implant 10. The first bit 224 rotationally couples the first drive member 116 to the first actuation assembly 260, whereby rotation of the first drive member 116 causes rotation of the first shaft 264 of the first actuation assembly 260. Rotation of the first shaft 264 causes movement of the proximal wedge assembly 282 and movement of the distal wedge assembly 284, thereby causing the inferior plate 250 and the superior plat 252 to move vertically upward and downward depending on the rotational direction of the first drive member 116.

During expansion and contraction of the first actuation assembly 260, the proximal wedge assembly 282 translates linearly along the first central shaft axis I due at least partially to the coupling between the threaded portion 274 of the drive shaft 264 and a threaded portion 279 of the proximal wedge assembly 282. A thread pitch of the threaded portion 274 of the first drive shaft 264 may be substantially similar to a thread pitch of the externally threaded portion 166 of the first traveler member 108. During expansion and contraction (e.g. during rotation of the first drive member 116, the first traveler member 108, and the first drive shaft 264), the first traveler member 108 and the first tether member 112 translate relative to the housing 102 a distance substantially similar to a distance the proximal wedge assembly 282 translates relative to the first drive shaft 264. The configurations of the threaded portion 274 of the first drive shaft 264 and the treaded portion 166 of the first traveler member 108 help maintain the coupling between the first tether member 112 and the first actuation assembly 260.

Figure 24:
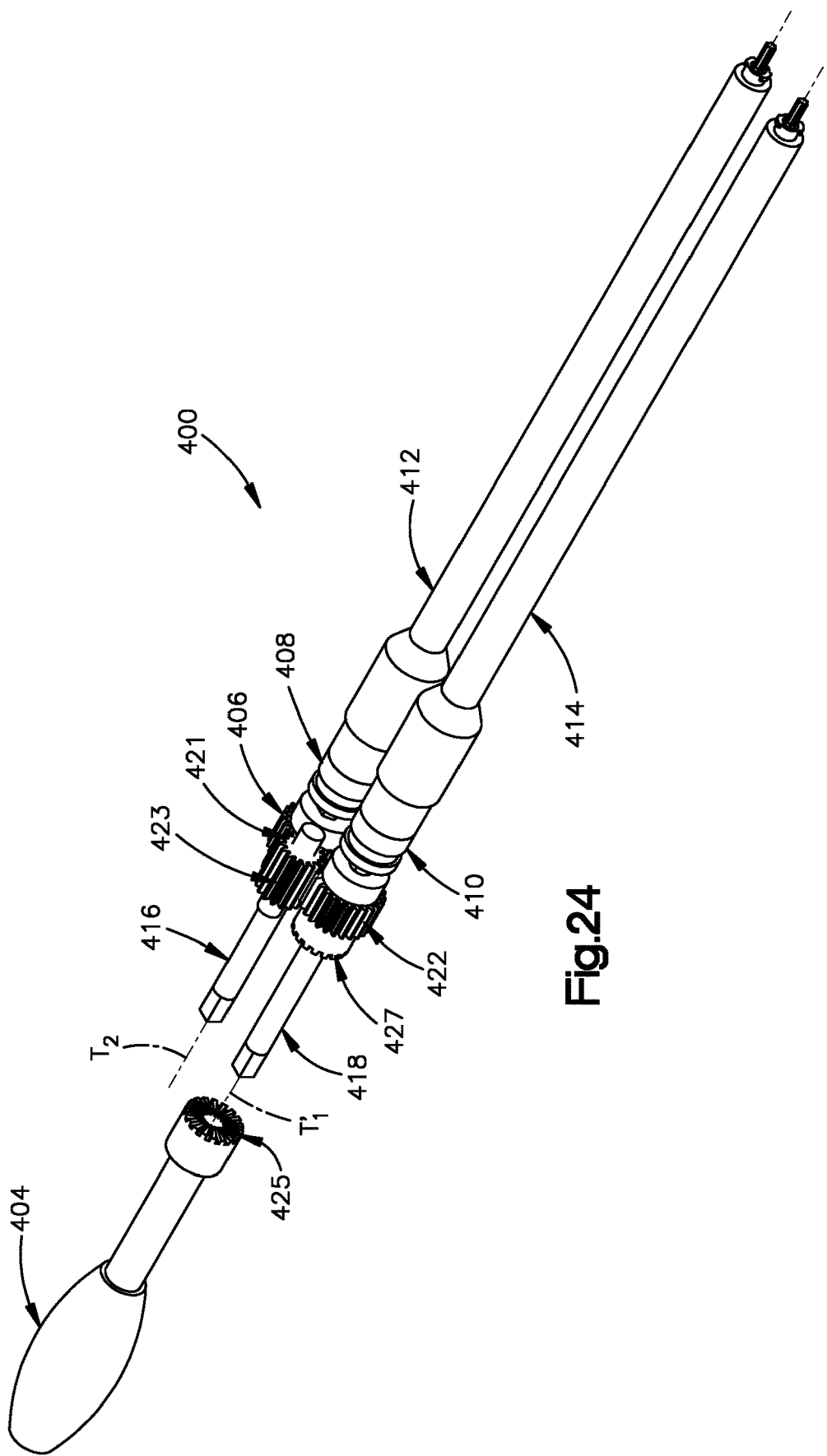
FIG. 24 illustrates a partially exploded perspective view of a second aspect of an implant adjustment tool, according to an aspect of this disclosure.
Figure 25:
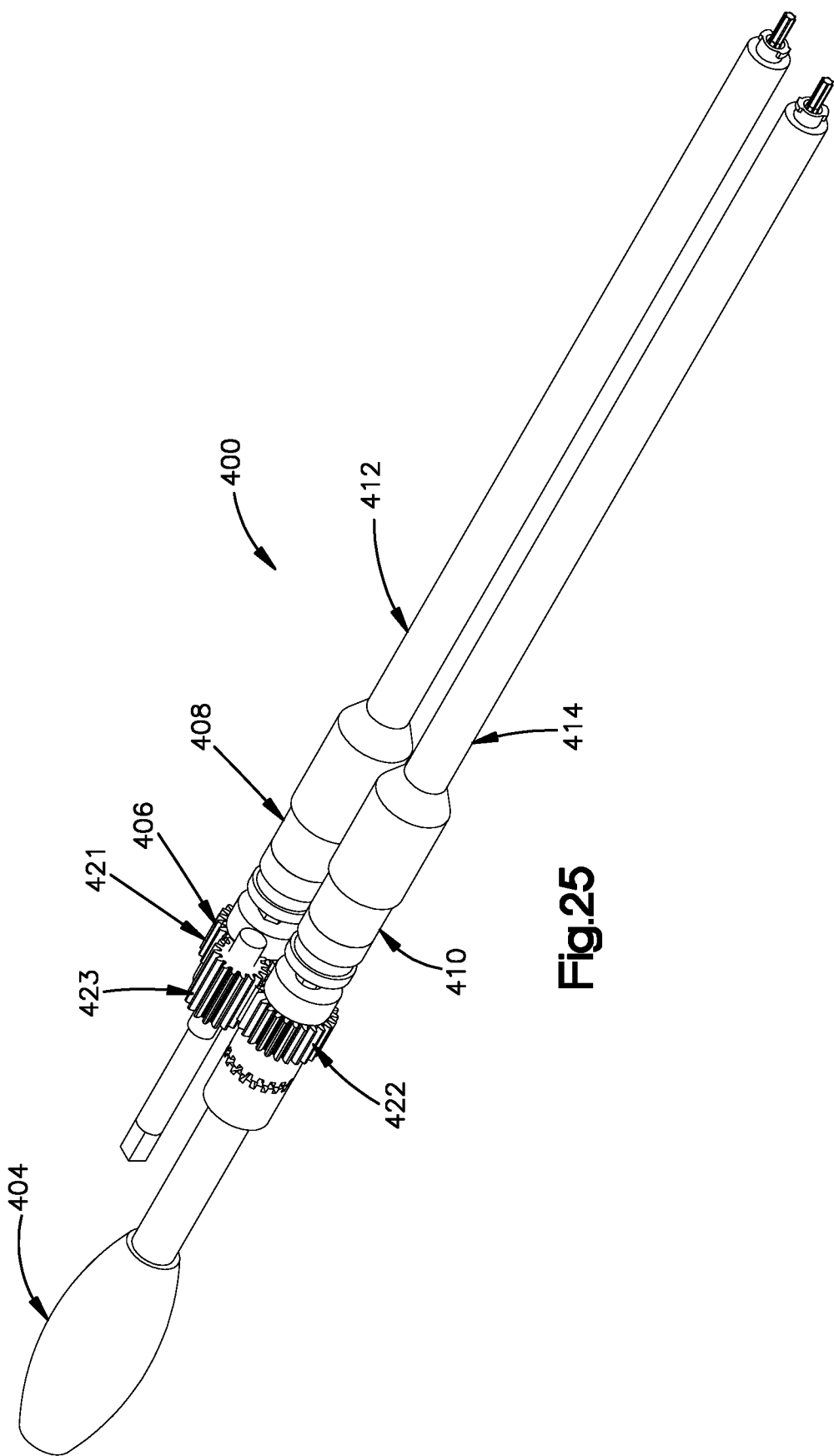
FIG. 25 illustrates a collapsed perspective view of the implant adjustment tool shown in FIG. 24.

FIG. 24 illustrates a first perspective view of an alternate aspect of a second adjustment tool 400, and FIG. 25 illustrates a second perspective view of an alternate aspect of the second adjustment tool 400, according to aspects of this disclosure. Portions of the alternate aspect of the adjustment tool 400 are similar to aspects of the adjustment tool 100 described above in FIGS. 2 through 16 and 20 through 23, and those portions function similarly to those described above. The second adjustment tool 400 includes a housing (not shown), a handle 404, a gear assembly 406, a first traveler member 408, a second traveler member 410, a first tether member 412, a second tether member 414, a first drive member 416, and a second drive member 418.

The gear assembly 406 includes a first gear member 421, a second gear member 422, and a third gear member 423. It will be appreciated that the gear assembly 406 may include additional gear members. The first gear member 421 is rotationally coupled to the first drive member 416 such that rotation of the first drive member 416 causes rotation of the first gear member 421. The first gear member 421 extends about an outer surface of the first drive member 416. The coupling between the first gear member 421 and the first drive member 416 may include, for example, a recess, a protrusion, a keyed portion, or other feature of the outer surface of the first drive member 416 that corresponds to a recess, a protraction, a keyed portion, or other feature on an inner surface of the first gear member 421.

The first gear member 421 is further rotationally coupled to the second gear member 422 via the third gear member 423. The first, second, and third gear members 421, 422, and 423 each include gear teeth configured and sized to engage with each of the other gears. For example, the gear teeth of the first gear member 421 include a height and/or a pitch that correspond to the gear teeth of the third gear member 423, such that rotation of the first gear member 421 causes a rotation of the third gear member 423. Similarly, the gear teeth of the third gear member 423 include a height and/or pitch that correspond to the gear teeth of the second gear member 422, such that rotation of the third gear member 423 causes a rotation of the second gear member 422.

The second gear member 422 is coupled to the second drive member 418 such that the second gear member rotates independently of the second drive member 418. For example, during rotation of only the second drive member 418, the second gear member 422 can remain substantially stationary. The second gear member 422 is further coupled to the first gear member 421 via the third gear member 423, such that rotation of the second gear member 422 causes rotation of the first gear member 421.

The handle 404 is configured to control the first and second drive members 416 and 418 and the gear assembly 406. The handle 404 is configured to removably engage and rotate each of the first and second drive members 116 and 118 individually and as a pair. The handle 404 can be rotationally coupled to the first drive member 416 such that rotation of the handle 404 causes rotation of the first drive member 416. The rotational coupling can be formed between an inner surface of the handle 404 and an outer surface of the first drive member 416 (e.g. corresponding recesses/protrusions, keyed portions, or other corresponding features on the inner handle surface and the outer drive member surface). When the handle 404 is rotationally coupled to the first drive member 416, rotation of the handle 404 about a first tool central axis $T_2$ causes rotation of the first drive member 416, thereby causing rotation of the first, second, and third gear members 421, 422, and 423. Since the second drive member 418 is not rotationally coupled to the second gear member 422, rotation of the first drive member 416 by the handle 404 does not cause the second drive member 418 to rotate.

The handle 404 can be rotationally coupled to the second drive member 418 such that rotation of the handle 404 causes rotation of the second drive member 418. FIG. 25 illustrates a perspective view of the adjustment tool 400 with the handle 404 engaged with the second drive member 418. The rotational coupling can be formed between an inner surface of the handle 404 and an outer surface of the second drive member 418 in a substantially similar manner as the handle 404 is coupled to the first drive member 416. When the handle 404 is rotationally coupled to the first drive member 416, the handle 404 can transition between a first position and a second position. In the first position of the handle 404, the handle 404 is rotationally coupled to the second drive member 418 such that rotation of the handle 404 about a second tool central axis $T'2$ causes rotation of the second drive member 418 about the second tool central axis $T'2$. Since the second drive member 418 is not rotationally coupled to the second gear member 422, rotation of the second drive member 418 by the handle 404 does not cause the second gear member 422 to rotate. In the second position of the handle 404, the handle 404 is rotationally coupled to the second drive member 418 and the handle 404 is also rotationally coupled to the second gear member 422. In the second position, rotation of the handle 404 about the second tool central axis $T'_2$ causes both the second drive member 418 and the second gear member 422 to rotate about the second tool central axis $T'_2$.

The handle 404 includes a handle coupling element 425. The handle coupling element 425 may include, for example, a toothed face. The second gear member 422 includes a drive coupling element 427. The drive coupling element 427 has a configuration that corresponds to the configuration of the handle coupling element 425 such that the drive coupling element 427 can couple to the handle coupling element 425. When the handle 404 is coupled to the second drive member 418, the handle coupling element 425 faces the drive coupling element 427. In the second position of the handle 404, the handle coupling element 425 is engaged with the drive coupling element 427, thereby rotationally coupling the handle 404 to the second gear member 422.

The handle 404 can be removed from the second drive member 418 and coupled to the first drive member 416, and vice versa. During use of the adjustment tool 400, the first and second drive members 416 and 418 can be individually rotated by the handle 404 and can also be rotated substantially simultaneously by the handle 404. For example, coupling the handle 404 to the first drive member 416 and rotating the handle 404 about the first tool central axis $T_2$ causes the first drive member 416 to rotate about the first tool central axis $T_2$, but does not cause the second drive member 418 to rotate. Coupling the handle 404 to the second drive member 418, positioning the handle 404 in the first position, and rotating the handle 404 about the second tool central axis $T'_2$ causes the second drive member 416 to rotate about the second tool central axis $T'_2$, but does not cause the first drive member 418 to rotate. Coupling the handle 404 to the second drive member 418, positioning the handle 404 in the second position, and rotating the handle 404 about the second tool central axis $T'_2$ causes the second drive member 416 to rotate about the second tool central axis T'$_2$ and also causes the first drive member 416 to rotate about the first tool central axis T$_2$ via the gear assembly 406.

It will be appreciated that rotation of the first and second drive members 416 and 418 may cause the respective first and second traveler members 408 and 410 and the respective first and second tether members 412 and 414 to rotate and/or translate in a substantially similar manner as the first and second drive members 116 and 118 cause the first and second traveler members 108 and 110 and the first and second tether members 112 and 114 of the adjustment tool 100 to rotate and/or translate.

It will be appreciated that the adjustment tool 400 may also include a housing (not shown). The housing may be configured substantially similarly to the housing 102 of the adjustment tool 100. Alternatively, the housing of the adjustment tool 400 may also include other components and/or features such as channels, compartments, or still other features to house, for example, the gear assembly 406 or other components of the adjustment tool 400.

Figure 26:
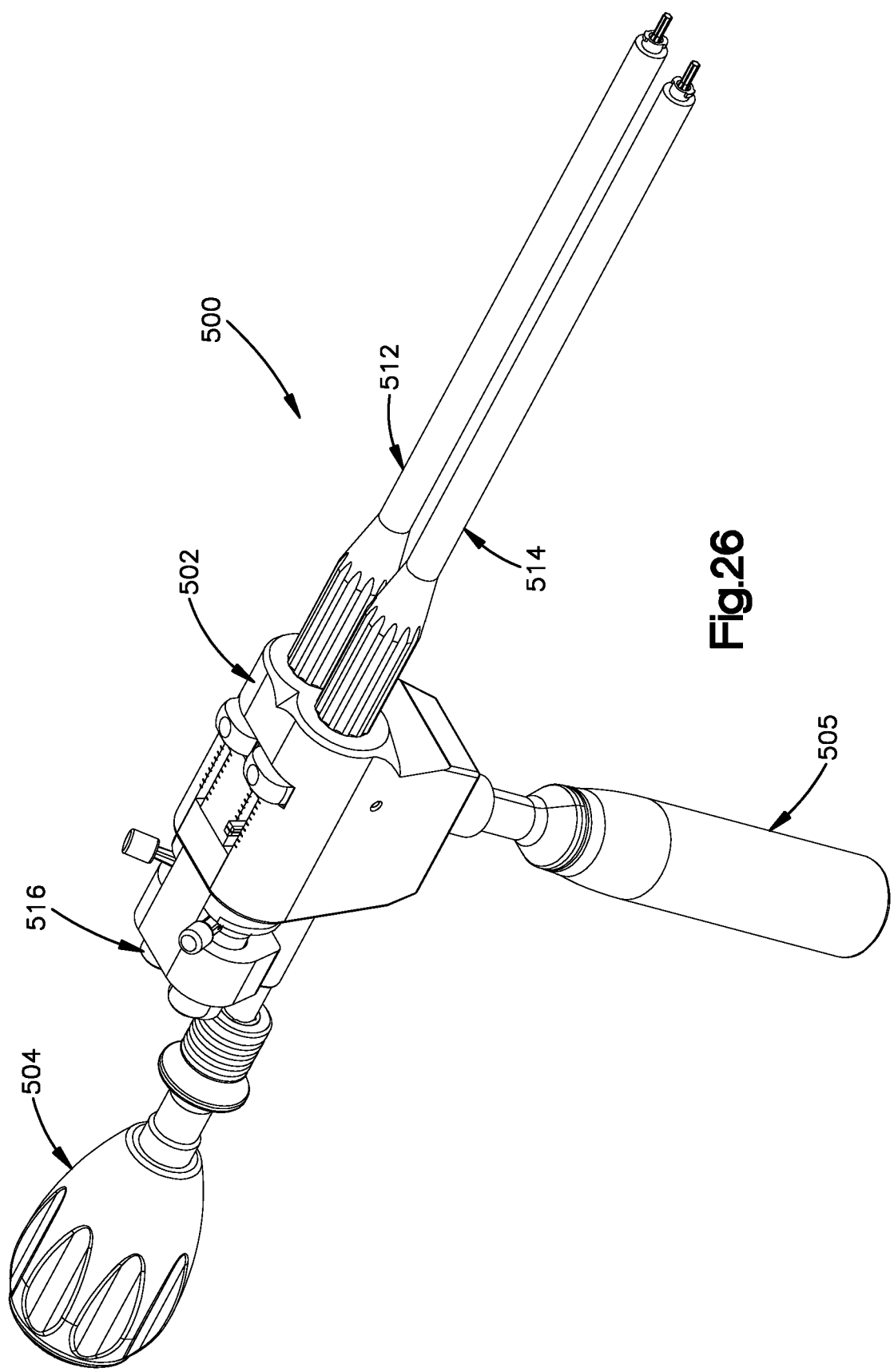
FIG. 26 illustrates a perspective view of a third aspect of an implant adjustment tool, according to an aspect of this disclosure.

FIG. 26 illustrates a perspective view of an alternate aspect of a third adjustment tool 500, according to an aspect of this disclosure. Portions of the alternate aspect of the adjustment tool 500 are similar to aspects of the adjustment tool 100 described above in FIGS. 2 through 16 and 20 through 23 and the adjustment tool 400 described above in FIGS. 24 and 25, and those portions function similarly to those described above.

Figure 27:
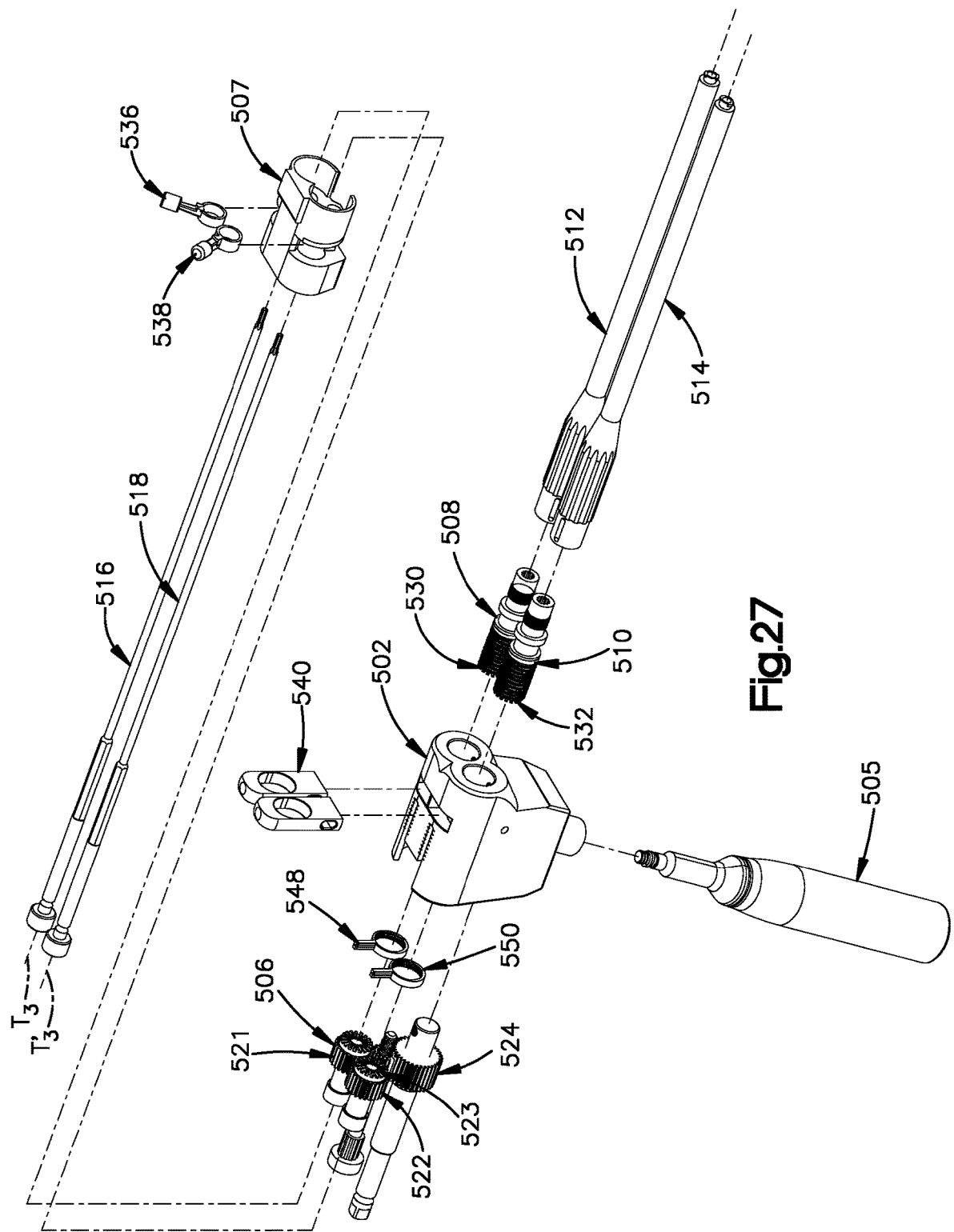
FIG. 27 illustrates a partially exploded perspective view of the third aspect of the adjustment tool shown in FIG. 26.

FIG. 27 illustrates a partially exploded perspective view of the third adjustment tool 500, according to an aspect of this disclosure. The third adjustment tool 500 includes a housing 502, a handle 504, a grip member 505, a gear assembly 506, a control housing 507, a first traveler member 508, a second traveler member 510, a first tether member 512, a second tether member 514, a first drive member 516, and a second drive member 518.

Figure 28:
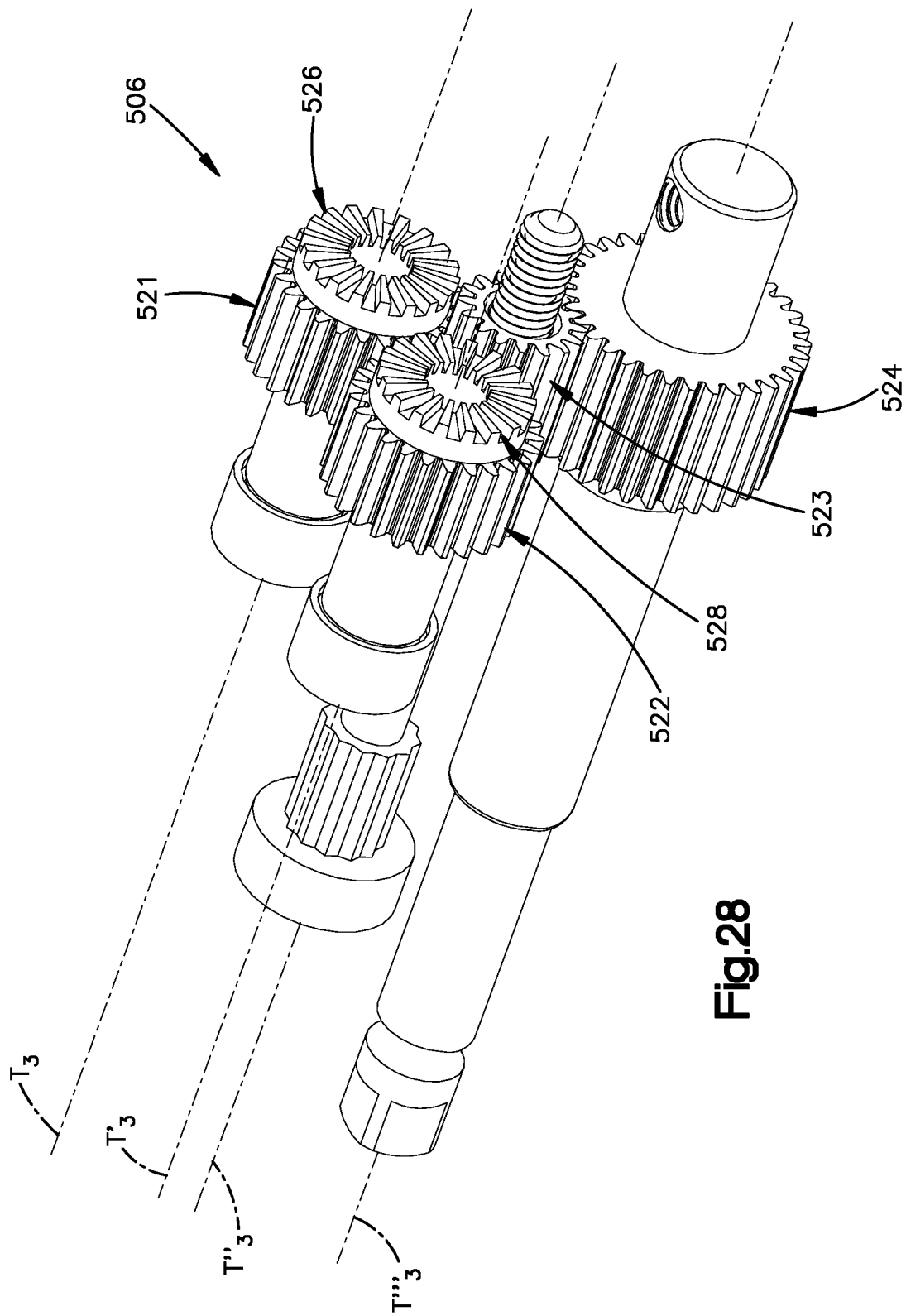
FIG. 28 a perspective view of a gear assembly of the implant adjustment tool shown in FIG. 26.

FIG. 28 illustrates a perspective view of the gear assembly 506, according to an aspect of this disclosure. The gear assembly 506 includes a first gear member 521, a second gear member 522, and a third gear member 523. The first gear member 521 is rotationally independent of the first drive member 516 such that rotation of the first drive member 516 about a first tool central axis T$_3$ does not cause rotation of the first gear member 521 about the first tool central axis T$_3$. The first gear member 521 extends about an outer surface of the first drive member 516. The coupling between the first gear member 521 and the first drive member 516 may include, for example, a recess, a protrusion, a keyed portion, or other feature of the outer surface of the first drive member 516 that corresponds to a recess, a protraction, a keyed portion, or other feature on an inner surface of the first gear member 521.

The first gear member 521 is further rotationally coupled to the second gear member 522 via the third gear member 523 (e.g. middle gear). The coupling between the first and third gears 521 and 523 is such that, for example, rotation of the first gear member 521 about the first tool central axis T$_3$ causes rotation of the third gear member 523 about a third tool central axis T"$_3$ in a direction opposite to a direction of rotation of the first gear member 521. Similarly, the coupling between the third gear and the second gear 523 and 522 is such that, for example, rotation of the third gear member 523 about the third tool central axis T"$_3$ causes rotation of the second gear member 522 about a second tool central axis T'$_3$ in a direction opposite to the direction of rotation of the third gear member 523.

The first, second, and third gear members 521, 522, and 523 each include gear teeth configured and sized to engage with each of the other gears. For example, the gear teeth of the first gear member 521 include a height and/or a pitch that correspond to the gear teeth of the third gear member 523, such that rotation of the first gear member 521 causes a rotation of the third gear member 523. Similarly, the gear teeth of the third gear member 523 include a height and/or pitch that correspond to the gear teeth of the second gear member 522, such that rotation of the third gear member 523 causes a rotation of the second gear member 522.

The second gear member 522 is rotationally coupled to the second drive member 518 such that rotation of the second drive member 518 about the second tool central axis T'$_3$ causes rotation of the second gear member 522 about the second tool central axis T'$_3$. The second gear member 522 extends about an outer surface of the second drive member 518. The coupling between the second gear member 522 and the second drive member 518 may include, for example, a recess, a protrusion, a keyed portion, or other feature of the outer surface of the second drive member 518 that corresponds to a recess, a protraction, a keyed portion, or other feature on an inner surface of the second gear member 522. The second gear member 522 is further coupled to the first gear member 521 via the third gear member 523, such that rotation of the second gear member 522 about the second tool central axis T'$_3$ causes rotation of the first gear member 521 about the first tool central axis T$_3$.

It will be appreciated that the gear assembly 506 may include additional gear members. For example, a fourth gear member 524 may be coupled to the third gear member 523. The coupling between the fourth gear member 524 is such that rotation of the fourth gear member 524 about a fourth central tool axis T'''$_3$ causes a rotation of the third gear 523 about the third tool central axis T"$_3$ in a direction opposite to the rotation of the fourth gear member 524. In an aspect, the first, second, third, and fourth central tool axes T$_3$, T'$_3$, T"$_3$, and T'''$_3$ are substantially parallel to each other.

The first and second gear members 521 and 522 further include a first coupling element 526 and a second coupling element 528, respectively. The first and second coupling elements 526 and 528 may include, for example, a toothed face, or other coupling element configured to couple the first and second gear members 521 and 522 to the first and second traveler members 508 and 510, respectively. Accordingly, the first and second traveler members 508 and 510 may include first and second gear coupling elements 530 and 532, respectively. The first and second gear coupling elements 530 and 532 being configured to interlock with the first and second coupling elements 526 and 528, respectively. In an aspect, the first coupling element 526 may face the first gear coupling element 530 along the first tool central axis T$_3$. Similarly, the second coupling element 528 may face the second gear coupling element 533 along the second tool central axis T'$_3$.

The first and second traveler members 508 and 510 are rotationally coupled to the first and second drive members 516 and 518, respectively, such that rotation of the first and second traveler members 508 and 510 cause rotation of the first and second drive members 516 and 518. The coupling between the first and second traveler members 508 and 510 and the respective first and second drive members 516 and 518 may include, for example, a recess, a protrusion, a keyed portion, or other feature of the outer surface of the first and second drive members 516 and 518 that corresponds to a recess, a protraction, a keyed portion, or other feature on an inner surface of the respective first and second traveler members 508 and 510.

Figure 29:
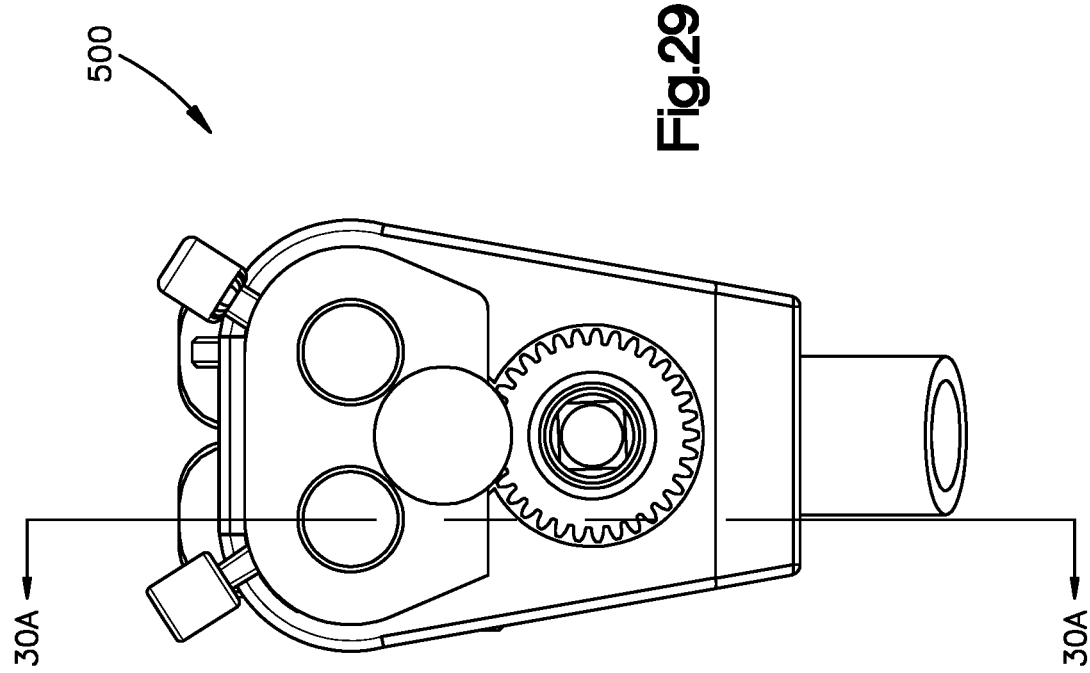
FIG. 29 illustrates a side elevation view of the implant adjustment tool shown in FIG. 26.
Figure 30A:
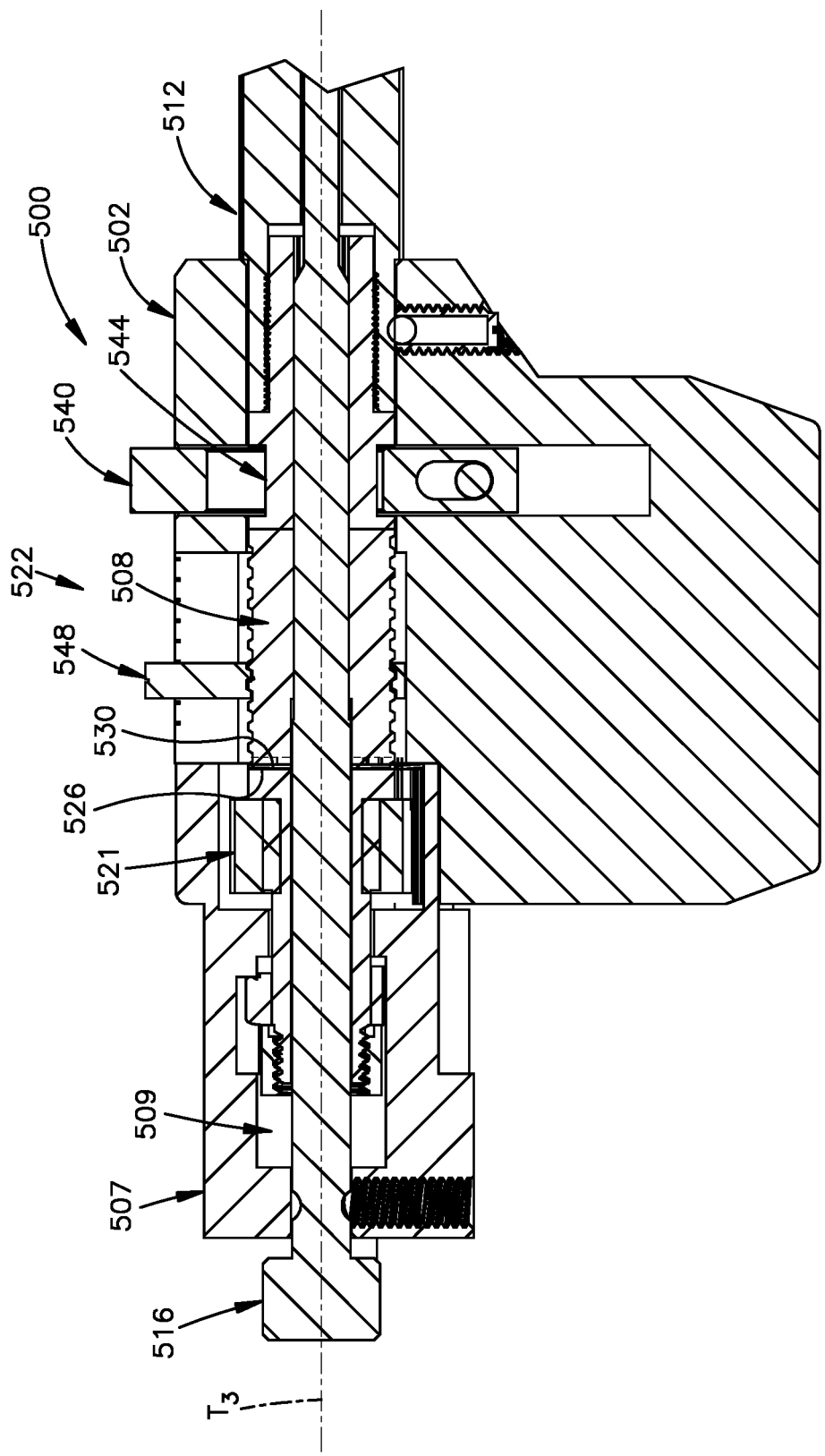
FIG. 30A illustrates a cross-sectional view of the implant adjustment system shown in FIG. 29 taken along line 30-30 showing a first position of the adjustment tool.
Figure 30B:
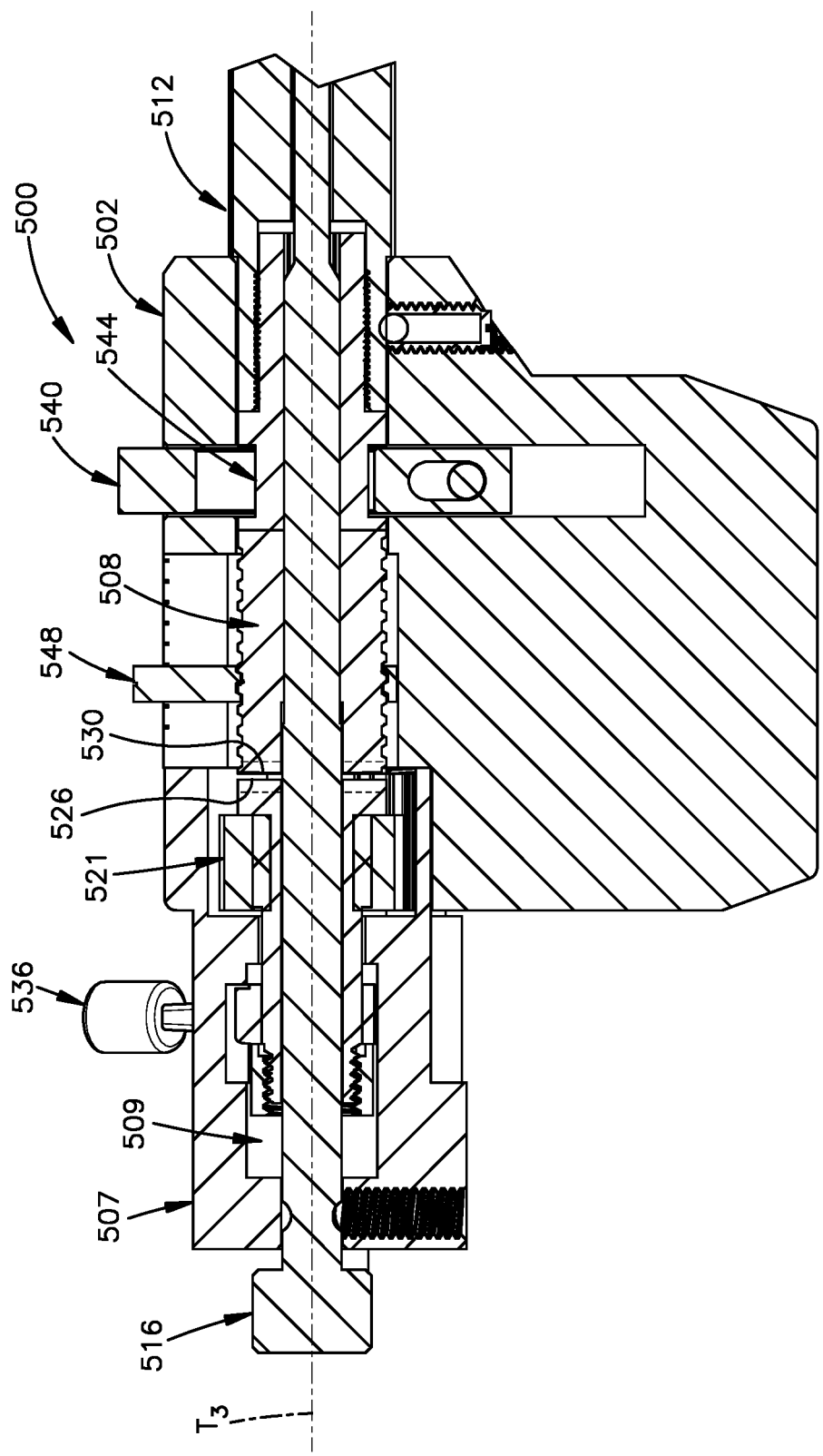
FIG. 30B illustrates a cross-sectional view of the implant adjustment system shown in FIG. 29 taken along line 30-30 showing a second position of the adjustment tool.

FIG. 29 illustrates a side elevation view of the implant adjustment tool 500, according to an aspect of this disclosure. FIG. 30A illustrates a cross-sectional view of a portion of the implant adjustment tool 500 taken along line 30-30 of FIG. 29 showing a first position (e.g. coupled position) of the first gear member 521. FIG. 30B illustrates a cross-sectional view of a portion of the implant adjustment tool 500 taken along line 30-30 of FIG. 29 showing a second position (e.g. de-coupled position) of the first gear member 521. The description provided below regarding the control of the adjustment tool 500 is with respect to the first drive assembly (e.g. the first traveler member 508, the first tether member 512, the first drive member 516, and the first gear member 521), however, it will be appreciated that the description may apply to the second drive assembly (e.g. the second traveler member 510, the second tether member 514, the a second drive member 518, and the second gear member 522) and/or any other drive assembly composing the adjustment tool 500.

The first gear member 521 is configured to transition between a first position and a second position. In the first position (e.g. FIG. 30A) of the first gear member 521, the first gear member 521 is rotationally coupled to the first traveler member 508, such that the first coupling element 526 of the first gear member 521 is interlocked with the first coupling element 530 of the first traveler member 508. The coupling between the first gear member 521 and the first traveler member 508 substantially rotationally fixes the first gear member 521 to the first traveler member 508 such that rotation of the first gear member 521 about the first central axis $T_3$ causes rotation of the first traveler member 508 about the first central axis $T_3$.

The first gear member 521 can be biased toward the first position by a resilient member (not shown) positioned within a cavity 509 of the control housing 507. For example, in the first position of the first gear member 521, the resilient member can provide a biasing force on the first gear member 521 in a direction parallel to the first central axis $T_3$. The biasing force causes the first coupling element 526 of the first gear member 521 to remain interlocked with the first coupling element 530 of the first traveler member 508.

In the second position (e.g. FIG. 30B) of the first gear member 521, the first gear member 521 is de-coupled from the first traveler member 508. For example, the first gear member 521 may be spaced apart from the first traveler member 508 along the first central axis $T_3$ such that the first coupling element 526 of the first gear member 521 is not interlocked with the first coupling element 530 of the first tether member 508. In the second position, the first gear member 521 rotates independently from the first tether member 508.

To transition the first gear member 521 between the first position and the second position, a first cam member 536 can be rotated about the first gear member 521 to translate the first gear member 521 along the first central axis $T_3$. The connection between the first cam member 536 and the first gear member 521 can be a cam-type connection, such that rotation of the first cam member 536 causes linear translation of the first gear member 521. Rotation of the first cam member 536 about the first central axis $T_3$ causes the resilient member positioned within the cavity 509 of the control housing 507 to expand and contract. For example, rotating the first cam member 536 about the first central axis $T_3$ in a first direction allows the resilient member to expand, thereby transitioning the first gear member 521 into the first position. Rotating the first cam member 536 about the first central axis $T_3$ in a second direction opposite the first direction causes the first gear member 521 to compress the resilient member within the cavity 509, thereby transitioning the first gear member 521 into the second position. It will be appreciated that a second cam member 538 can be rotated about the second gear member 522 to transition the second gear member 522 between first and second positions in substantially the same manner as the first cam member 536 transitions the first gear member 521.

The first traveler member 508 can be linearly fixed within the housing 502, and capable of rotating independently of the housing 502. The first traveler member 508 may be substantially retained within the housing 502 by a first tether lock 540. The first tether lock 540 can be inserted into a lock recess 544 defined by an outer surface of the first tether member 508 to substantially prevent linearly translation of the first traveler member 508 within the housing 502. The first tether lock 540 can be transitioned between a locked configuration, in which the first tether lock 540 is received within the lock recess 544, and an unlocked configuration, in which the first tether lock 540 is spaced away from the lock recess 544. In the unlocked configuration of the first tether lock 540, the first tether member 508 can be inserted and removed from the housing 502 during assembly and disassembly, respectively.

The first traveler member 508 is threadedly coupled to the first tether member 512. The coupling between the first traveler member 508 and the first tether member 512 is such that rotation of the first traveler member 508 about the first central axis $T_3$ causes linear translation of the first tether member 512 along the first central axis $T_3$. A pitch of the threaded coupling between the first traveler member 508 and the first tether member 512 can be configured to be substantially the same as a pitch of the threaded coupling between the first actuator 264 and the first expansion wedge 282 of the implant 10. The substantially similar pitches result in the translation of the first tether member 512 relative to the first traveler member 508 to be substantially similar to the translation of the first expansion wedge 282 relative to the first actuator 264. For example, during control of the implant 10 to expand, rotation of the first tether member 508 about the first central axis $T_3$ causes 1.) the first drive member 516 to rotate about the first central axis $T_3$ (e.g. when the first gear member 521 is in the first position), thereby causing the first tether member 512 to translate distally along the first central axis $T_3$, and 2.) the first actuator 264 of the implant 10 to rotate about the first central shaft axis I, thereby causing the first expansion wedge 282 to translate distally along the first central shaft axis I. The substantially similar pitches cause the first tether member 512 to translate a substantially similar distance along the first central axis $T_3$ as the first expansion wedge 282 translates along the first central shaft axis I.

The implant adjustment tool 500 can also include first and second counter member 548 and 550. The counter members 548 and 550 are configured to engage an outer surface of the first and second tether members 508 and 510, respectively. The counter members 548 and 550 are configured to threadedly engage with the respective first and second tether members 508 and 510 such that rotation of the first and second tether members 508 and 510 causes linearly translation of the respective counter members 548 and 550 along the first central axis $T_3$. At least a portion of each of the counter members 548 and 550 can be visible from an exterior of the housing 502. During use of the implant adjustment tool 500, an operator can determine an amount of expansion of the first and second actuation assemblies 260 and 262 of the implant 10 based on the linear translation of the respective counter members 548 and 550.

It is appreciated that adjustment tool 500 provides the physician with enhanced freedom regarding the sequencing of achieving the desired expansion and/or lordosis of the implant 10. In particular, after predetermining the desired amount of expansion and/or lordosis of the implant 10 in the intervertebral space 5, the physician can insert the implant 10 in the collapsed configuration into the intervertebral space 5 along the medial-lateral direction, as shown in FIG. 1. If both expansion and lordosis are desired, the physician can expand the implant 10 uniformly to a partially expanded configuration, and then expand or retract the implant 10 in a non-uniform manner to achieve the desired lordotic angle of the implant 10. The implant 10 can be expanded or retracted non-uniformly in various ways, including, for example: operating one of the first and second actuation assemblies 260 and 262 independently; or operating both of the first and second actuation assemblies 260 and 262 simultaneously, as further described below.

With reference to FIGS. 17-19 and 27, during an physical procedure, the physician can couple the first and second tether members 512 and 514 of the implant adjustment tool 500 to the respective first and second actuation assemblies 260 and 262 of the implant 10. When the first and second tether members 512 and 514 are coupled to the respective first and second actuation assemblies 260 and 262, the first drive member 516 engages the first actuator 264 and the second drive member 518 engages the second actuator (not visible in figures). Rotation of the respective first and second drive members 516 and 518 causes the implant 10 to expand and collapse, as explained above with reference to the control of the implant 10 by the adjustment tool 100.

The physician can select between various modes of operation of the adjustment tool 500 using the first and second cam members 536 and 538. For example, the first cam member 536 can be rotated to transition the first gear member 521 between the first and second positions. Similarly, the second cam member 538 can be rotated to transition the second gear member 521 between the first and second positions. Control of the first and second cam members 536 and 538 can toggle the adjustment tool 500 between a first drive mode A, a second drive mode B, a third drive mode C, and a fourth drive mode D. In the first drive mode A, the adjustment tool 500 can be set to only operate the first drive member 516. The first cam member 536 can be rotated such that the first gear member 521 is in the first position, thereby coupling the first gear member 521 to the first traveler member 508. The second cam member 538 can be rotated such that the second gear member 522 is in the second position, thereby de-coupling the second gear member 522 from the second traveler member 510. In the first drive mode A, when the physician rotates the fourth gear member 524, the first and second gear members 521 and 522 are rotated, but since the first gear member 521 is coupled to the first traveler member 508 and the second gear member 522 is de-coupled from the second traveler member 510, only the first traveler member 508 rotates. The rotation of the first traveler member 508 causes the first drive member 516 to rotate, which causes the first tether member 512 to linearly translate and the first actuation assembly 260 to rotate.

In the second drive mode B, the adjustment tool 500 can be set to only operate the second drive member 518. The first cam member 536 can be rotated such that the first gear member 521 is in the second position, thereby de-coupling the first gear member 521 from the first traveler member 508. The second cam member 538 can be rotated such that the second gear member 522 is in the first position, thereby coupling the second gear member 522 to the second traveler member 510. In the second drive mode B, when the physician rotates the fourth gear member 524, the first and second gear members 521 and 522 are rotated, but since the first gear member 521 is de-coupled from the first traveler member 508 and the second gear member 522 is coupled to the second traveler member 510, only the second traveler member 510 rotates. The rotation of the second traveler member 510 causes the second drive member 518 to rotate, which causes the second tether member 514 to linearly translate and the second actuation assembly 262 to rotate.

In the third drive mode C, the adjustment tool 500 can be set to operate both of the first and second drive member 516 and 518. The first cam member 536 can be rotated such that the first gear member 521 is in the first position, thereby coupling the first gear member 521 to the first traveler member 508. The second cam member 538 can be rotated such that the second gear member 522 is in the first position, thereby coupling the second gear member 522 to the second traveler member 510. In the third drive mode C, when the physician rotates the fourth gear member 524, the first and second gear members 521 and 522 are rotated, and since both of the first and second gear members 521 and 522 are coupled to the first and second traveler members 508 and 510, respectively, both of the first and second traveler members 508 and 510 rotate. The rotation of the first traveler member 508 causes the first drive member 516 to rotate, which causes the first tether member 512 to linearly translate and the first actuation assembly 260 to rotate. Similarly, the rotation of the second traveler member 510 causes the second drive member 518 to rotate, which causes the second tether member 514 to linearly translate and the second actuation assembly 262 to rotate. The rotation of the first and second traveler members 508 and 510 can occur substantially simultaneously.

In the fourth drive mode D, the adjustment tool 500 can be set such that neither the first nor the second drive member 516 and 518 operate. The first cam member 536 can be rotated such that the first gear member 521 is in the second position, thereby de-coupling the first gear member 521 from the first traveler member 508. The second cam member 538 can be rotated such that the second gear member 522 is in the second position, thereby de-coupling the second gear member 522 from the second traveler member 510. In the fourth drive mode D, when the physician rotates the fourth gear member 524, the first and second gear members 521 and 522 are rotated, but since neither the first nor the second gear member 521 and 522 are coupled to the respective first and second traveler members 508 and 510, neither the first nor the second traveler member 508 and 510 rotates. The fourth drive mode D can be used during insertion and extraction of the implant 10 during a physical procedure, thereby reducing the likelihood that inadvertent rotation of the fourth gear member 524 causes actuation of the first and second actuation assemblies 260 and 262.

The design of the adjustment tool 500, as disclosed herein allows the physician to utilize any of the foregoing modes of expansion, contraction and/or lordosis to achieve the final desired configuration, and to adjust the configuration of the implant 10 as necessary, including during subsequent physical procedures on the patient.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A tool configured to insert and adjust an intervertebral implant, the adjustment tool comprising:
   a housing;
   a traveler coupled to the housing;
   a tether coupled to the traveler such that rotation of the traveler relative to the housing causes linear movement of the tether relative to the housing, the tether having a distal end configured to couple to the intervertebral implant; and
   a drive member configured to couple to the traveler such that rotation of the drive member causes rotation of the traveler relative to the housing,
   wherein the drive member is configured to transition between a first position and a second position, the drive member coupled to the tether in the first position such that rotation of the drive member causes rotation of the tether relative to the traveler.

2. The tool of claim 1, wherein the tether is substantially linearly fixed to the traveler, and the traveler is threadedly coupled to the housing.

3. The tool of claim 1, wherein the drive member is coupled to the traveler in the second position.

4. The tool of claim 3, wherein the traveler defines a traveler channel that extends through the traveler, and wherein a proximal end of the tether is coupled to the traveler.

5. The tool of claim 4, wherein an outer surface of the drive member includes a coupling element, wherein in the second position of the drive member, the coupling element is coupled to an inner surface of the traveler channel such that the drive member is substantially rotatably fixed to the traveler.

6. The tool of claim 5, wherein in the first position of the drive member, the coupling element is coupled to an inner surface of the tether channel such that the drive member is substantially rotatably fixed to the tether.

7. The tool of claim 4, wherein the housing defines a housing channel that extends through the housing, and wherein the tether defines a tether channel that extends through the tether from a proximal tether opening to a distal tether opening, the drive member being positioned within the housing channel, the traveler channel, and the tether channel such that in the first position of the drive member, the drive member extends through the housing channel and the traveler channel and into the tether channel such that a distal end of the drive member is located between the proximal tether opening and the distal tether opening, and in the second position of the drive member, the drive member extends through the housing channel, the traveler channel, and the tether channel such that a proximal end and the distal end of the drive member are both external to the housing channel, the traveler channel, and the tether channel.

8. The tool of claim 3, wherein the drive member transitions between the first position and the second position by a linear movement of the drive member relative to the housing, traveler, and the tether.

9. The tool of claim 1, wherein the traveler is a first traveler, the tether is a first tether, and the drive member is a first drive member, wherein the adjustment tool further comprises:
   a second traveler coupled to the housing;
   a second tether coupled to the second traveler such that rotation of the second traveler relative to the housing causes linear movement of the second tether relative to the housing; and
   a second drive member configured to couple to the second traveler such that rotation of the second drive member causes rotation of the second traveler relative to the housing.

10. A tool configured to insert and adjust an intervertebral implant, the tool comprising:
    a housing defining first and second housing channels that extend therethrough;
    a first drive member configured to be received through the first housing channel, the first drive member having a proximal end with a first engagement surface configured to be rotationally driven, and a distal end configured to engage the implant;
    a second drive member configured to be received through the second housing channel, the second drive member having a proximal end with a second engagement surface configured to be rotationally driven, and a distal end configured to engage the implant;
    a tether having a distal end configured to couple to the intervertebral implant, wherein the tether is rotatable relative to the housing,
    wherein the first drive member is configured to transition between a first position and a second position, the first drive member coupled to the tether in the first position such that rotation of the first drive member causes rotation of the tether relative to the housing, the first drive member decoupled from the tether in the second position such that the drive member is rotatable relative to the tether, and
    wherein the distal end of the first drive member is distal to the distal end of the tether in the second position.

11. The tool of claim 10, further comprising a traveler coupled to the housing, wherein the tether is substantially linearly fixed to the traveler, and the traveler is threadedly coupled to the housing.

12. The tool of claim 11, wherein the drive member is coupled to the traveler in the second position.

13. The tool of claim 12, wherein the traveler defines a traveler channel that extends through the traveler, and wherein a proximal end of the tether is coupled to the traveler.

14. The tool of claim 13, wherein an outer surface of the first drive member includes a coupling element, wherein in the second position of the first drive member, the coupling element is coupled to an inner surface of the traveler channel such that the first drive member is substantially rotatably fixed to the traveler.

15. The tool of claim 13, wherein the housing defines a housing channel that extends through the housing, and wherein the tether defines a tether channel that extends through the tether from a proximal tether opening to a distal tether opening, the first drive member being positioned within the housing channel, the traveler channel, and the tether channel such that in the first position of the first drive member, the first drive member extends through the housing channel and the traveler channel and into the tether channel such that a distal end of the first drive member is located between the proximal tether opening and the distal tether opening, and in the second position of the first drive member, the first drive member extends through the housing channel, the traveler channel, and the tether channel such that a proximal end and the distal end of the first drive member are both external to the housing channel, the traveler channel, and the tether channel.

16. The tool of claim 15, wherein in the first position of the drive member, the coupling element is coupled to an inner surface of the tether channel such that the drive member is substantially rotatably fixed to the tether.

17. The tool of claim 12, wherein the drive member transitions between the first position and the second position by a linear movement of the drive member relative to the housing, traveler, and the tether.

18. The tool of claim 12, wherein the traveler is a first traveler, the tether is a first tether, and the adjustment tool further comprises:
   a second traveler coupled to the housing; and
   a second tether coupled to the second traveler such that rotation of the second traveler relative to the housing causes linear movement of the second tether relative to the housing,
   wherein the second drive member is configured to couple to the second traveler such that rotation of the second drive member causes rotation of the second traveler relative to the housing.

* * * * *